United States Patent
Kudo

(10) Patent No.: US 10,390,790 B2
(45) Date of Patent: Aug. 27, 2019

(54) RADIOGRAPHIC IMAGING APPARATUS AND METHOD, AND CONSOLE DEVICE

(71) Applicant: FUJIFILM Corporation, Tokyo (JP)

(72) Inventor: Yoshimitsu Kudo, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 16/015,390

(22) Filed: Jun. 22, 2018

(65) Prior Publication Data

US 2018/0317874 A1 Nov. 8, 2018

Related U.S. Application Data

(62) Division of application No. 15/164,026, filed on May 25, 2016, now Pat. No. 10,022,105.

(30) Foreign Application Priority Data

Jun. 5, 2015 (JP) ................. 2015-114764

(51) Int. Cl.
*A61B 6/00* (2006.01)
*G08B 29/18* (2006.01)
*H04W 24/04* (2009.01)
*G08B 5/36* (2006.01)
*G08B 21/18* (2006.01)

(52) U.S. Cl.
CPC ............ *A61B 6/586* (2013.01); *A61B 6/4283* (2013.01); *A61B 6/563* (2013.01); *G08B 5/36* (2013.01); *G08B 21/185* (2013.01); *G08B 29/185* (2013.01); *H04W 24/04* (2013.01)

(58) Field of Classification Search
CPC ....... A61B 6/4283; A61B 6/563; A61B 6/586; G08B 29/185; H04W 24/04
See application file for complete search history.

(56) References Cited

U.S. PATENT DOCUMENTS

2009/0201841 A1 8/2009 Tachikawa
2010/0013657 A1 1/2010 Ohta
(Continued)

FOREIGN PATENT DOCUMENTS

JP 2014-147789 A 8/2014

*Primary Examiner* — Chih-Cheng Kao

(74) *Attorney, Agent, or Firm* — Sughrue Mion, PLLC

(57) ABSTRACT

A radiographic imaging apparatus includes an electronic cassette and a console device for radio communication with the electronic cassette. The electronic cassette includes a transmitter for transmitting a beacon for the radio communication. A regulation unit regulates beaconing of the beacon in a predetermined specific state among plural operational states. The console device includes a receiver for receiving the beacon. A communication failure detector checks whether a communication failure has occurred in the radio communication according to a receiving state of the beacon in the receiver. A display panel or speaker generates alert notification to notify the communication failure assuming that the communication failure detector judges that the communication failure has occurred. An operational state detector checks whether the electronic cassette is in the specific state. An alert manager avoids generation of the alert notification while the operational state detector judges that the electronic cassette is in the specific state.

17 Claims, 24 Drawing Sheets

(56) References Cited

U.S. PATENT DOCUMENTS

2013/0134316 A1    5/2013   Nakatsugawa
2013/0195251 A1    8/2013   Saigusa
2016/0095567 A1*   4/2016   Tachikawa ............. A61B 6/465
                                                       378/98.2

* cited by examiner

| REQUEST ID | OD0001 |
| --- | --- |
| CASE ID | P0500 |
| BODY PART/POSTURE/DIRECTION | CHEST/SITTING/AP |

REQUEST FOR IMAGING

| IMAGING CONDITION (MENU) | EXPOSURE CONDITION |
| --- | --- |
| CHEST/LYING/AP | TUBE VOLTAGE 100 kV, TUBE CURRENT 200 mA, EXPOSURE TIME 20 msec |
| CHEST/LYING/PA | TUBE VOLTAGE 120 kV, TUBE CURRENT 220 mA, EXPOSURE TIME 25 msec |

RADIOGRAPHIC IMAGING APPARATUS AND METHOD, AND CONSOLE DEVICE

CROSS-REFERENCE TO RELATED APPLICATION

This application is a Divisional Application of U.S. application Ser. No. 15/164,026, filed May 25, 2016, which claims priority under 35 USC 119 from Japanese Patent Application No. 2015-114764, filed 5 Jun. 2015, the disclosures of each of which are incorporated by reference herein.

BACKGROUND OF THE INVENTION

1. Field of the Invention

The present invention relates to a radiographic imaging apparatus and method and a console device. More particularly, the present invention relates to a radiographic imaging apparatus and method and a console device in which a problem of occurrence of a communication failure can be coped with suitably to continue radiographic imaging smoothly in a workflow.

2. Description Related to the Prior Art

A radiographic imaging apparatus or system, or X-ray imaging apparatus or system is known in the field of the medical diagnosis for imaging of a patient body by use of radiation or X-rays. The radiographic imaging apparatus includes a radiographic imaging device (apparatus) or X-ray imaging device (apparatus), and a console device or system terminal device. The radiographic imaging device detects (generates) a radiation image according to X-rays transmitted through the patient body or object. The console device communicates with the radiographic imaging device for transmitting various data and the radiation image.

A sensor panel or detection panel is incorporated in the radiographic imaging device, for example, a flat panel detector (FPD). Numerous pixels are arranged in the sensor panel and store charge upon receiving X-rays or radiation transmitted through the patient body. The sensor panel reads out the charge stored in the pixels, converts the charge into an image signal, and outputs a radiation image.

Well-known examples of the radiographic imaging device include an installed type and a portable type. The installed type is installed with a floor stand or patient table disposed in an examination room for radiographic imaging. The portable type has a portable housing and the sensor panel contained in the housing. The portable type of the radiographic imaging device is referred to as an electronic cassette for radiographic imaging. The electronic cassette as a mobile device can be carried to various locations in a hospital facility other than the examination room. For example, the electronic cassette is utilized for mobile imaging, namely, for imaging in a patient room for a patient who cannot walk to the examination room. Also, the electronic cassette may be used in various sites external to the hospital facility, for example, in a home of an elderly patient for home care services, in an emergency site of an accident or disaster where injury of a patient should be cared.

For the mobile imaging, a doctor, technician or operator positions the electronic cassette relative to the patient body, for example, sets the electronic cassette between the lying patient body and the bed, makes the patient hold the electronic cassette manually, or the like. Assuming that a cable is physically connected to the electronic cassette for communication with the console device, the cable is likely to obstruct smooth handling of the electronic cassette. In view of this problem, various ideas for wireless connection for the electronic cassette to the console device have been suggested, for example, in JP-A 2014-147789.

In general, a wireless access point (AP) is used for radio communication between wireless terminal devices. The wireless access point always generates a beacon or radio wave at a constant beacon interval, for example, 100 msec. The beacon is a signal for notifying the presence of the wireless access point to the wireless terminal devices located nearby. Even after establishing the communication link between the wireless terminal devices, the wireless access point continues generating the beacon.

The embodiments of JP-A 2014-147789 include a structure of an electronic cassette (sensor unit) having a function of the wireless access point. A radio communication unit of the electronic cassette transmits the beacon and functions as the wireless access point.

The electronic cassette is influenced by noise of radio waves because of an electronic device. Assuming that noise of radio waves occurs in image readout to converting charge of pixels into an image signal in the sensor panel, the noise is superimposed with a radiation image to create degradation in its image quality. The wireless access point always generates the beacon in the structure incorporated in the electronic cassette, so that the beacon may cause the degradation. In view of such a problem, JP-A 2014-147789 suggests detection of completion of the image readout before beaconing, and delay of the beaconing in the case of an incomplete state of the image readout.

The beaconing is regulated in a predetermined specific state among plural operational states of the electronic cassette which has the function of the wireless access point as disclosed in the embodiments of JP-A 2014-147789. For example, the beaconing is delayed assuming that the image readout is incomplete. However, a problem arises with the regulation of the beacon.

A difficulty occurs in reception of the beacon at a console device while the electronic cassette regulates the beaconing in the specific state. Even though no communication failure has occurred in the reception of the beacon during the regulation, false alert may be generated because of improper judgment of disconnection with the electronic cassette on the basis of a false communication failure. An operator becomes notified of the false alert of the communication failure by the console device.

Upon the occurrence of the alert after the communication failure in the console device, he or she must perform tasks unrelated to the radiographic imaging, such as responding to the alert, and checking a cause of the communication failure. It is likely to take waiting time to patients with objects to be imaged, to lower efficiency in the imaging remarkably specially during the operator's tasks for recovery after the alert.

SUMMARY OF THE INVENTION

In view of the foregoing problems, an object of the present invention is to provide a radiographic imaging apparatus and method and a console device in which a problem of occurrence of a communication failure can be coped with suitably to continue radiographic imaging smoothly in a workflow.

In order to achieve the above and other objects and advantages of this invention, a radiographic imaging apparatus including an electronic cassette and a console device for radio communication with the electronic cassette is provided. The electronic cassette includes a transmitter for transmitting a beacon for the radio communication. A regulation unit regulates beaconing of the beacon in a predetermined specific state among plural operational states. The console device includes a receiver for receiving the beacon. A communication failure detector checks whether a communication failure has occurred in the radio communication according to a receiving state of the beacon in the receiver. An alert indicator generates alert notification to notify the communication failure assuming that the communication failure detector judges that the communication failure has occurred. An operational state detector checks whether the electronic cassette is in the specific state. An alert manager avoids generation of the alert notification while the operational state detector judges that the electronic cassette is in the specific state.

Preferably, while the operational state detector judges the specific state, the alert manager disables the communication failure detector.

In another preferred embodiment, while the operational state detector judges the specific state, the alert manager disables the alert indicator.

Preferably, information of a timeout period is stored previously, and the communication failure detector detects the communication failure assuming that interruption of reception of the beacon in the receiver has continued for the timeout period.

Preferably, the timeout period is set longer while the electronic cassette is in the specific state than while the electronic cassette is in a non-specific state different from the specific state.

Preferably, the electronic cassette includes a sensor panel having pixels for storing charge by detecting radiation transmitted through an object. The specific state is a state of image readout in which the sensor panel reads out the charge from the pixels for conversion into an image signal.

Preferably, information of a timeout period is stored previously, and the communication failure detector detects the communication failure assuming that interruption of reception of the beacon in the receiver has continued for the timeout period. The timeout period is changed according to time taken for the image readout.

Preferably, the electronic cassette is a selected one of at least a first electronic cassette and a second electronic cassette of which the time for the image readout is longer than the first electronic cassette. The timeout period associated with the second electronic cassette is longer than the timeout period associated with the first electronic cassette.

In one preferred embodiment, the specific state is a state of movement of the electronic cassette.

In another preferred embodiment, the specific state is a sleep state in which part of circuit devices in the electronic cassette is powered.

Preferably, in the specific state, the regulation unit turns off the beacon.

Preferably, the regulation unit sets a beacon interval of the beacon longer while the electronic cassette is in the specific state than while the electronic cassette is in a non-specific state different from the specific state.

In still another preferred embodiment, the regulation unit sets a radio signal strength of the beacon lower while the electronic cassette is in the specific state than while the electronic cassette is in a non-specific state different from the specific state.

Preferably, the electronic cassette detects a start of exposure of radiation, and the transmitter transmits a radiation image of an object to the receiver upon the exposure of the object to the radiation. The specific state is a state in a period from monitoring for detecting the start of the exposure of the radiation until transmission of the radiation image.

In another preferred embodiment, the electronic cassette detects an end of exposure of radiation, and the transmitter transmits a radiation image of an object to the receiver upon the exposure of the object to the radiation. The specific state is a state in a period from the detected end of the exposure of the radiation until transmission of the radiation image.

Also, a radiographic imaging method in which radio communication is performed between an electronic cassette and a console device includes a step of transmitting a beacon for the radio communication from the electronic cassette. Beaconing of the beacon is regulated in the electronic cassette in a predetermined specific state among plural operational states. The beacon is received in the console device. It is checked whether a communication failure has occurred in the radio communication in the console device according to a receiving state of the beacon in the receiver. Alert notification is generated to notify the communication failure in the console device assuming that it is judged in the failure checking step that the communication failure has occurred. It is checked whether the electronic cassette is in the specific state in the console device. Generation of the alert notification is avoided in the console device while it is judged in the state checking step that the electronic cassette is in the specific state.

Also, a console device for radio communication with an electronic cassette includes a receiver for receiving a beacon from the electronic cassette. A communication failure detector checks whether a communication failure has occurred in the radio communication according to a receiving state of the beacon in the receiver. An alert indicator generates alert notification to notify the communication failure assuming that the communication failure detector judges that the communication failure has occurred. An operational state detector checks whether the electronic cassette is in a predetermined specific state among plural operational states in relation to the beacon. An alert manager avoids generation of the alert notification while the operational state detector judges that the electronic cassette is in the specific state.

Consequently, a problem of occurrence of a communication failure can be coped with suitably to continue radiographic imaging smoothly in a workflow, because the generation of the alert notification can be blocked in consideration of a specific state of the electronic cassette.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

First Embodiment

Figure 1:
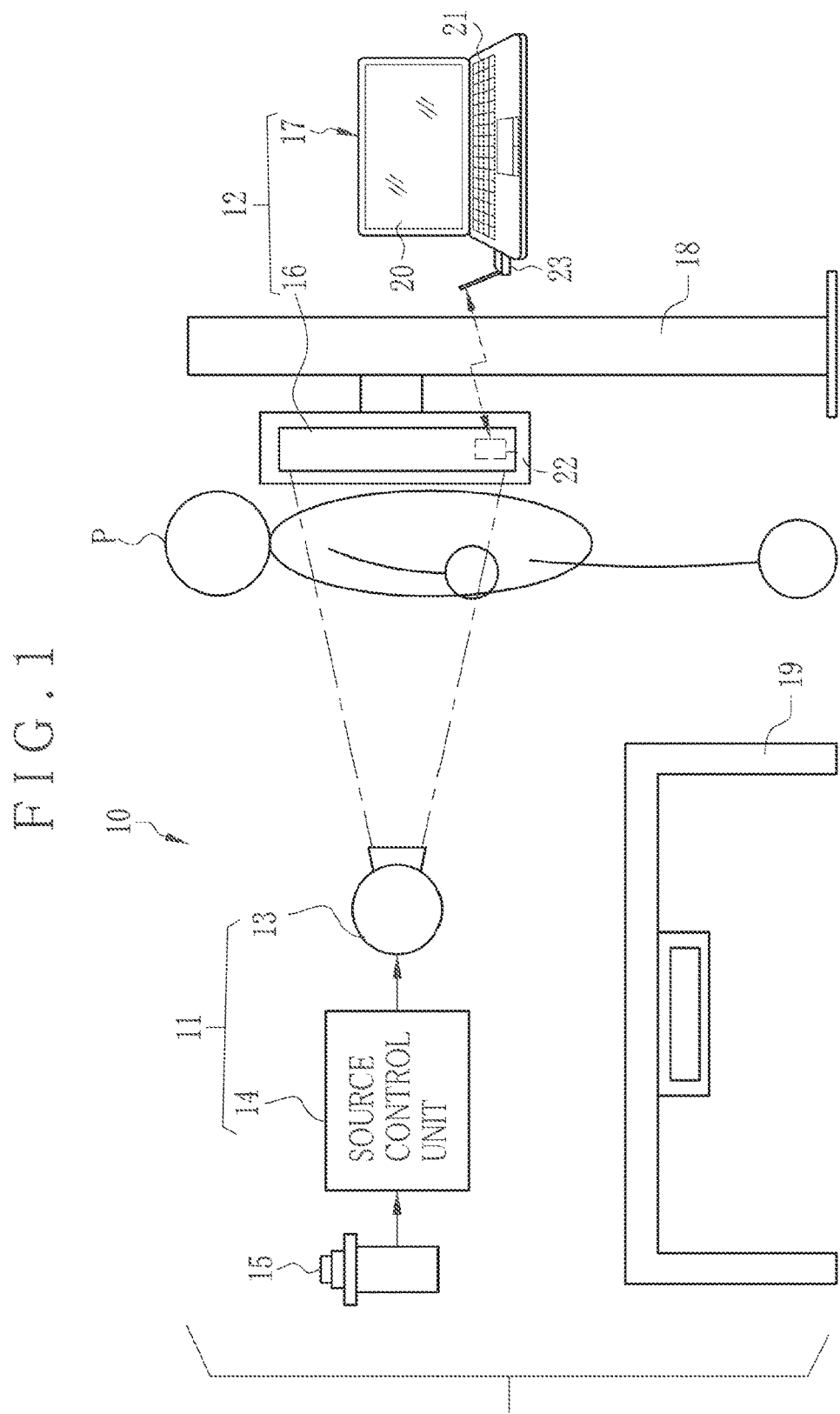
FIG. 1 is an explanatory view in a side elevation, illustrating a radiographic imaging system.

In FIG. 1, a radiographic imaging system 10 or X-ray imaging system includes a radiation generator 11, and a radiographic imaging apparatus 12 or X-ray imaging apparatus, and is installed in a storage room of a radiology department in a hospital facility. The radiation generator 11 includes a radiation source 13 or X-ray source and a source control unit 14. A radiation switch 15 is connected to the source control unit 14. The radiographic imaging apparatus 12 includes an electronic cassette 16 for radiographic imaging, and a console device 17 or system terminal device.

The examination room contains the radiographic imaging system 10, a floor stand 18 for radiographic imaging, and a patient table 19 for radiographic imaging. The floor stand 18 is used for imaging a patient body P in a standing posture (upright posture). The patient table 19 is used for imaging the patient body P in a lying posture. The radiation source 13 is used commonly in combination with the floor stand 18 and the patient table 19. In FIG. 1, the electronic cassette 16 is set on the floor stand 18 for radiographic imaging of the patient body P in the standing posture.

The radiation source 13 includes an X-ray tube and a collimator. The X-ray tube emits X-rays. The collimator or a field limiting device limits an exposure field of exposure of the X-rays to the patient P. The source control unit 14 controls a tube voltage and tube current for the X-ray tube, and exposure time of the X-rays. A storage area in the source control unit stores a plurality of exposure conditions according to respective body parts, such as a chest and abdomen, the exposure conditions including the tube voltage, tube current and exposure time. A desired one of the exposure conditions are selected and entered by an input of the operator.

The radiation switch 15 is manually operated by the operator for starting irradiation of X-rays. The radiation switch 15 is a two-step type. In case the radiation switch 15 is depressed halfway at a first depth (step), the source control unit 14 causes the radiation source 13 to perform preparation for irradiation of X-rays. In case the radiation switch 15 is depressed fully at a second depth, the source control unit 14 starts the radiation source 13 to emit X-rays. A timer is incorporated in the source control unit 14 for starting measuring time upon the start of the irradiation. Assuming that the measured time becomes equal to a preset exposure time according to the exposure condition, the radiation source 13 is stopped from emitting X-rays.

The electronic cassette 16 detects a radiation image from X-rays transmitted through the patient body P after generation from the radiation source 13. The console device 17 is constituted by a computer and programs installed therein. Examples of the computer are a notebook personal computer and the like. The programs include control programs and application programs. The control programs are an Operating System (OS) and the like. The console device 17 includes a display panel 20 or alert indicator, and an input panel 21 or user input interface, such as a touchscreen device, keyboard and the like. The console device 17 causes the display panel 20 to display various control pages with functions according to the GUI (graphical user interface), and receives inputs from the input panel 21 with the operator by use of the control pages.

The electronic cassette 16 has a first radio communication unit 22 or transmitter for a radiation image. The console device 17 has a second radio communication unit 23 (terminal) or receiver, which communicates with the first radio communication unit 22 wirelessly.

Figure 2:
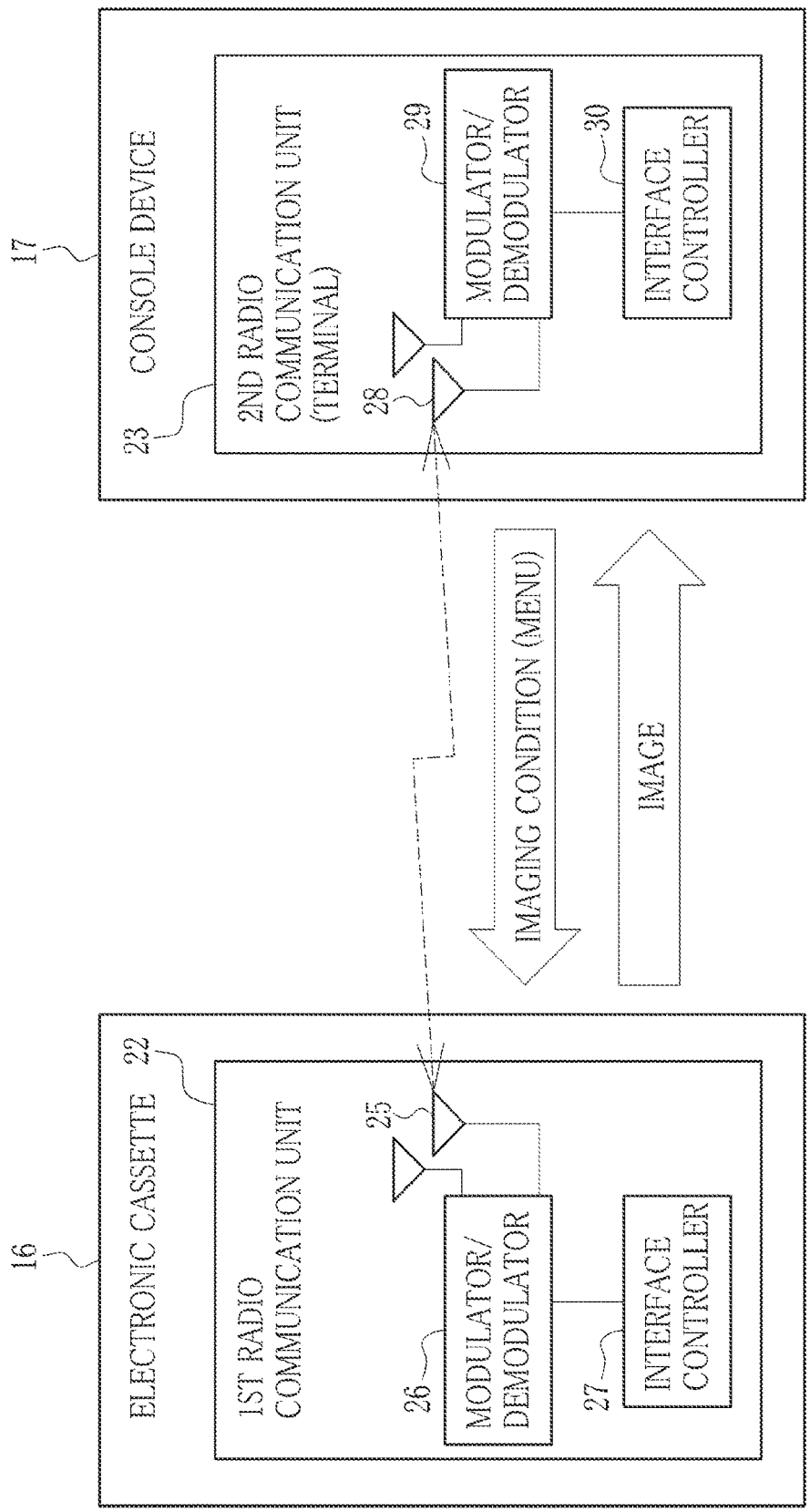
FIG. 2 is a block diagram schematically illustrating radio communication units.

In FIG. 2, the radio communication units 22 and 23 in the electronic cassette 16 and the console device 17 transmit data to one another, the data including an imaging condition (menu for the object), other information, radiation image, and the like.

The first radio communication unit 22 includes a communication antenna 25, a modulator/demodulator 26 and an interface controller 27 (transmission controller). The modulator/demodulator 26 performs modulation of data by combining the data with a carrier or wave, and performs demodulation to retrieve the data from the carrier received by the antenna 25. The interface controller 27 controls the transmission according to the standards of the wireless LAN (Local Area Network). Specifically, the interface controller 27 operates according to a communication protocol of TCP/IP (Transmission Control Protocol/Internet Protocol), or according to a communication protocol of IEEE 802.11n (IEEE being the Institute of Electrical and Electronics Engineers, Inc.).

Also, the second radio communication unit 23 is constituted by a communication antenna 28, a modulator/demodulator 29 and an interface controller 30 (transmission controller). Those are structurally the same as the antenna 25, the modulator/demodulator 26 and the interface controller 27 in the first radio communication unit 22.

The communication protocols are in plural layers according to the reference model of the Open Systems Interconnection (OSI). The communication is performed by a combined use of a plurality of communication protocols with a difference in the layer. TCP/IP is a communication protocol used also for the wired LAN, and used as a higher layer in the wireless LAN. IEEE 802.11n is a communication protocol in a layer directly lower than the TCP/IP, and determines a process of the communication of a wireless form.

There is no cable connected physically in the radio communication unlike the wired communication. The radio communication units 22 and 23 are required to perform logical connection with one another. To this end, the first radio communication unit 22 operates as a wireless access point (AP). The electronic cassette 16 corresponds to a parent device in the wireless LAN. The second radio communication unit 23 establishes the communication link with the first radio communication unit 22 operating as the wireless access point. The console device 17 corresponds to a child device in the wireless LAN.

In general, a wireless access point discrete from the wireless terminal devices is used for radio communication between the wireless terminal devices. However, the first radio communication unit 22 in the embodiment operates as the wireless access point. Thus, radio communication between the electronic cassette 16 and the console device 17 can be performed without using a wireless access point discrete from the electronic cassette 16 and the console device 17.

Figure 3:
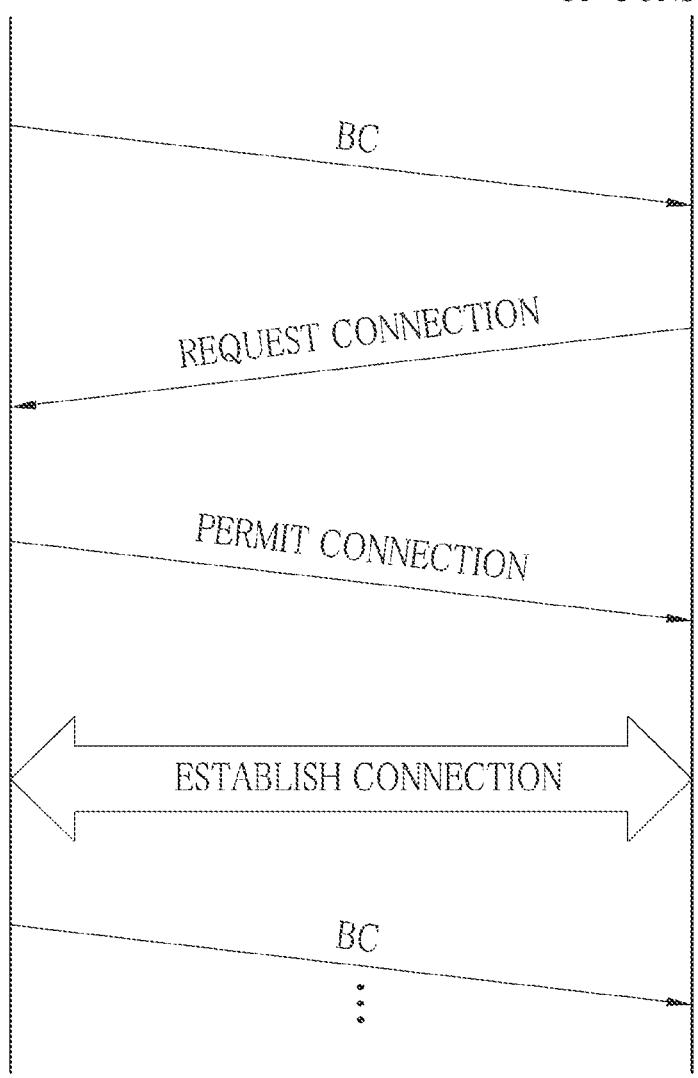
FIG. 3 is a timing chart illustrating a connecting sequence of the radio communication units.

In FIG. 3, a connecting sequence defined in the IEEE 802.11n for use between the radio communication units 22 and 23 is illustrated. Although the example is the IEEE 802.11n herein, other wireless LAN standards can be used, such as the IEEE 802.11a, IEEE 802.11b and IEEE 802.11ac of a new generation.

The first radio communication unit 22 in an active state in FIG. 3 emits a beacon BC or radio waves at a predetermined interval as long as 100 msec. The first radio communication unit 22 corresponds to a transmitter of the invention.

The beacon BC is a signal of notifying presence of the electronic cassette 16 to the console device 17. The console device 17 always monitors reception of the beacon BC with the second radio communication unit 23 during the operation. Assuming that the console device 17 is disposed in a coverage area of (reach of) the beacon BC, the second radio communication unit 23 can receive the beacon BC. In short, the second radio communication unit 23 is a receiver in the present invention. The first radio communication unit 22 transmits the beacon BC at a radio signal strength in the coverage area with a radius of 5 meters about the first radio communication unit 22.

Data in the beacon BC includes a network identifier, such as SSID (Service Set Identifier) and ESSID (Extended Service Set Identifier). The network identifier is specific information allocated to the first radio communication unit 22, a network having the first radio communication unit 22, or the like, for recognition from the second radio communication unit 23.

The network identifier of the first radio communication unit 22 of the electronic cassette 16 is registered in the second radio communication unit 23. The second radio communication unit 23 upon receiving the beacon BC having the predetermined network identifier generates a request for connection. The first radio communication unit 22 receives the request for connection, and performs verification for the console device 17 as a requester of the request. For this purpose, the second radio communication unit 23 transmits the request inclusive of verification information, such as a password.

The first radio communication unit 22 upon receiving the connection request performs verification by checking the received password and a predetermined password, and transmits information of permission to the second radio communication unit 23 assuming that the password is verified. A logical communication link is established between the electronic cassette 16 and the console device 17 upon receiving the information of the permission, to connect the console device 17 to the electronic cassette 16 for communication.

The first radio communication unit 22 continues emitting the beacon BC even after establishing the connection with the second radio communication unit 23. The wireless connection between the electronic cassette 16 and the console device 17 is continued while the second radio communication unit 23 receives the beacon BC from the first radio communication unit 22, and terminated upon interruption of reception of the beacon BC in the second radio communication unit 23. Examples the interruption of the reception include turn-off of the beacon BC in the first radio communication unit 22, external location of the console device 17 out of a coverage area of (the reach of) the beacon BC, and the like. However, the connecting sequence described above is performed again for performing reconnection, for example, upon a restart of emitting the beacon BC in the first radio communication unit 22, upon entry of the console device 17 in the coverage area of the beacon BC, or upon other events of possibility of receiving the beacon BC in the second radio communication unit 23.

The console device 17 receives an input of an imaging request for instructing the operator to perform the imaging. The request is input to the console device 17 by the RIS (Radiology Information System) which is not shown.

Figures 4, 5, 6:
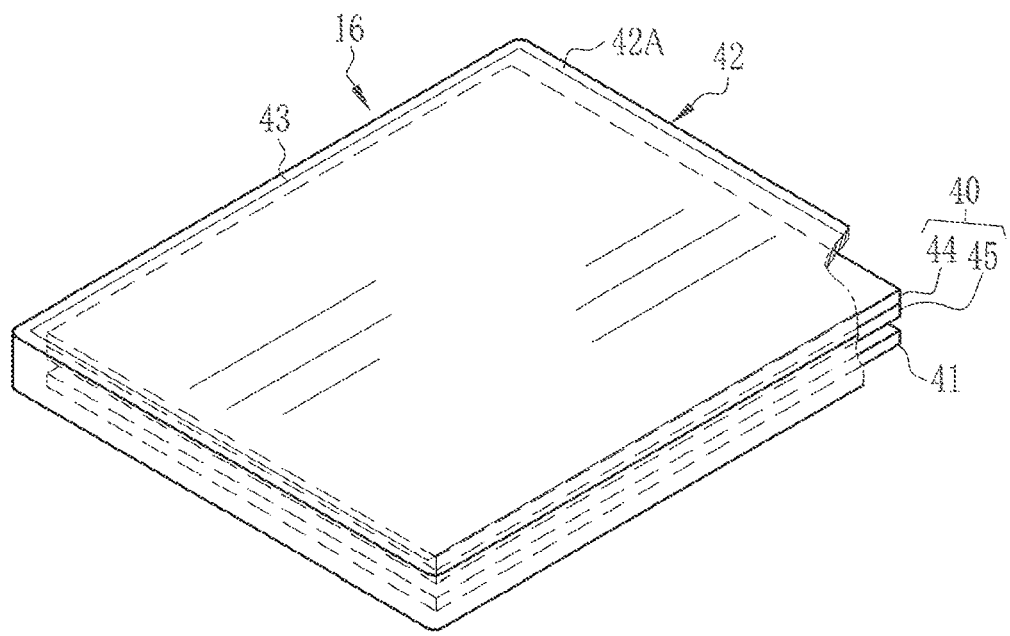
FIG. 4 is a data chart illustrating a request for imaging.
FIG. 5 is a table illustrating an exposure condition table.
FIG. 6 is a perspective view illustrating an electronic cassette.

In FIG. 4, the information of the request for imaging includes data items of a request ID (identification data), case ID, body part, posture, imaging direction, and the like. The request ID is alphanumeric information or signs for identifying each request for imaging, and allocated by the RIS automatically. A case ID of the patient P to be imaged is registered in the data item of the case ID. The case ID is alphanumeric information or signs for identifying each patient P.

Information of the body part, posture and imaging direction designated by a doctor having issued the request for imaging is recorded in data items of the body part, posture and imaging direction. Examples of the body parts are a head, cervical spine, chest, abdomen, hands, fingers, elbows, knees and the like. Examples of the postures of the patient P are a standing posture, lying posture, sitting posture and the like. Examples of the imaging directions of the patient P are an anteroposterior direction (AP), lateromedial direction, posteroanterior direction (PA) and the like. Furthermore, data items of personal information (not shown) are included in the imaging request, such as a name, sex, age, height and weight of the patient P. It is additionally possible to provide other data items associated with the imaging request, such as information of a hospital department or doctor as a requester of the imaging request, a data and time of receiving the imaging request in the RIS, purposes for imaging, a message from the doctor to a radiologist, or the like. The purposes include observation of a progress after the surgery, observation of effect of a drug for treatment, and the like.

Only one request for imaging can be issued for one patient P. Sometimes a plurality of requests for imaging may be issued simultaneously for one patient P. For this situation, recognition information is added to the request IDs of the plural requests for imaging, to express the association with the single patient P.

In FIG. 5, an exposure condition table 32 is stored in the console device 17. The exposure condition table 32 contains registered data of an imaging condition (menu for the object) and exposure condition associated therewith. The imaging condition is a set of a body part in a patient body, posture of the patient body, and imaging direction. Note that an imaging condition according to the embodiment can include the body part and imaging direction without including the posture, or can be a special imaging condition (menu for the object) corresponding to a tomosynthesis imaging or other special imaging.

The console device 17 is operated by the operator to cause the display panel 20 to display a request list in which requests for imaging in FIG. 4 are listed. The operator views the request list and checks the requests. Then the console device 17 drives the display panel 20 to display the information in the exposure condition table 32 in a form with a settable imaging condition (menu for the object). The operator selects one of the imaging conditions for coincidence in the body part, posture and imaging direction designated by the request for imaging.

As illustrated in FIG. 2, the console device 17 transmits the request ID, the console ID, the selected imaging condition and the exposure condition to the electronic cassette 16 by use of the second radio communication unit 23, the console ID being alphanumeric expressions or signs for identification, the selected imaging condition being set by the operator OP, the exposure condition corresponding to the selected imaging condition.

The console device 17 provides an image file of the radiation image in a form according to the standards of the DICOM (Digital Imaging and Communication in Medicine), and transmits the image file to the PACS (Picture Archiving and Communication System) which is not shown. The image file includes various data portions, such as the radiation image, a request ID, personal information, imaging condition (menu for the object), exposure condition, cassette ID and other meta information, which are associated together by use of one image ID. The cassette ID is alphanumeric information or signs for identifying the electronic cassette 16. A doctor of a hospital department after issuing the imaging request is enabled to download the image file by access to the PACS from a terminal device in the hospital department, so as to view the radiation image.

In FIG. 6, the electronic cassette 16 includes a sensor panel 40 or detection panel, a circuit board 41 and a portable housing 42, which contains those elements and has a quadrilateral form. The portable housing 42 has a size according to the International Standards ISO (International Organization for Standardization) 4090:2001 in the same form as a film cassette, IP cassette (imaging plate cassette), CR cassette (computed radiography cassette) and the like. In addition to the sensor panel 40 and the circuit board 41, the portable housing 42 contains the first radio communication unit 22, a battery, a wired communication interface and the like. The battery powers various elements in the electronic cassette 16. The wired communication interface is used for connection to the console device 17 with a cable. In case the first radio communication unit 22 is used, the electronic cassette 16 is driven by power from the battery and operated in a cableless manner.

The portable housing 42 has a quadrilateral opening formed in a front surface 42A, and a radio transparent plate 43 fitted in the quadrilateral opening. The electronic cassette 16 is so positioned as to direct the radiation source 13 to the front surface 42A. Also, various elements (not shown) are included in the portable housing 42, such as a switch for turning on and off a main power source, an indicator for informing an operational state of the electronic cassette 16, for example, available time of use of the battery, a state of readiness for imaging, and the like.

The sensor panel 40 includes a scintillator 44 and a photosensitive plate 45. The scintillator 44 and the photosensitive plate 45 are arranged in a direction toward the rear with reference to the front surface 42A where the X-rays are incident. The scintillator 44 contains phosphor CsI:Tl (thallium activated cesium iodide), $Gd_2O_2S$:Tb or GOS (terbium activated gadolinium oxysulfide), and the like, and converts incident X-rays through the radio transparent plate 43 into visible light for emission of the light. Note that a sensor panel can be so structured that the photosensitive plate 45 and the scintillator 44 are arranged in the direction toward the rear with reference to the front surface 42A. Also, a sensor panel can be a direct converting type for converting X-rays into signal charge directly by use of amorphous selenium as a photoconductive layer.

The photosensitive plate 45 detects visible light from the scintillator 44 and converts the same into an image signal. The circuit board 41 controls the operation of the photosensitive plate 45, and produces a radiation image according to the image signal output by the photosensitive plate 45.

Figure 7:
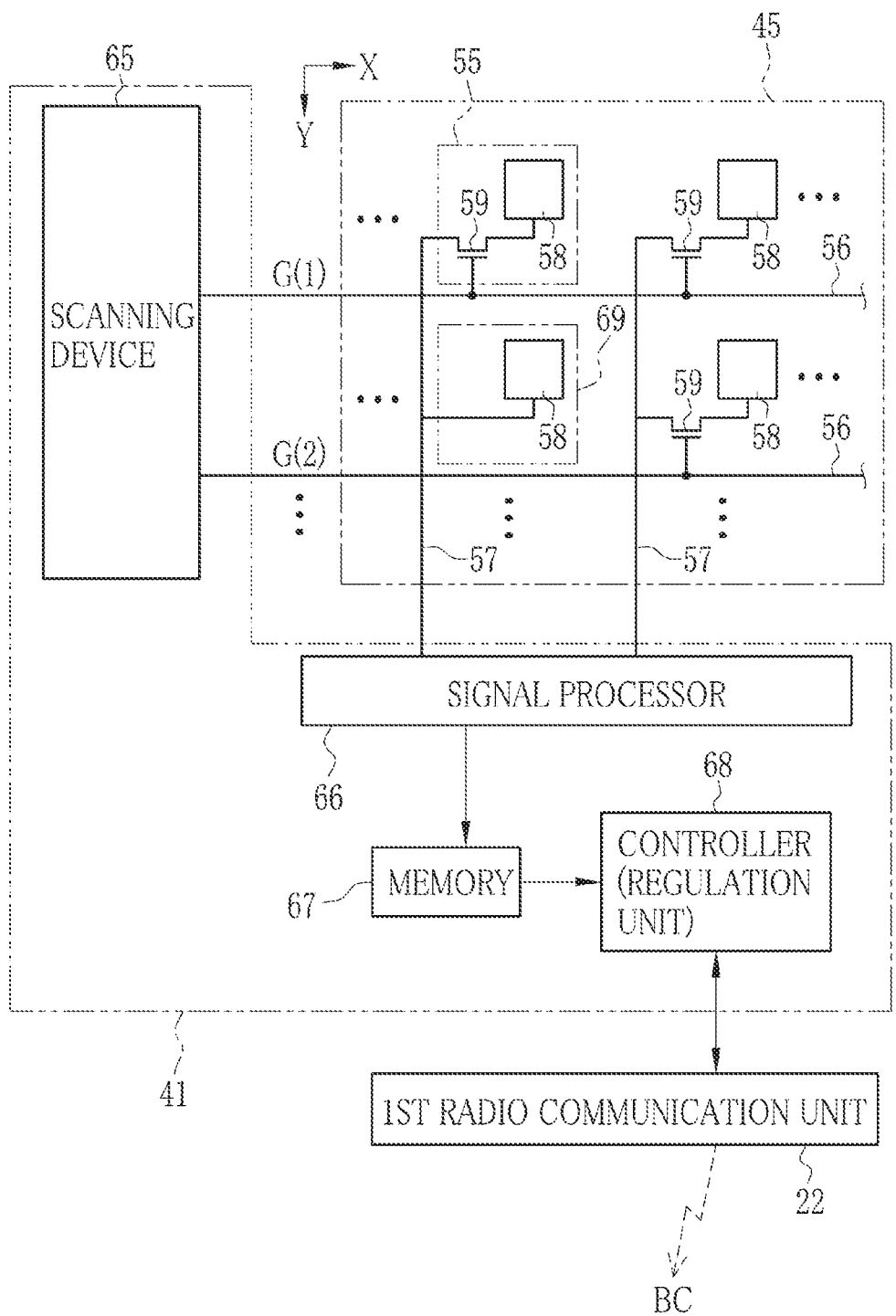
FIG. 7 is a block diagram schematically illustrating the electronic cassette.

In FIG. 7, the photosensitive plate 45 includes numerous pixels 55, N scan lines 56 and M signal lines 57. The pixels 55 are arranged in a matrix form of N×M on a substrate of glass (not shown). The scan lines 56 extend in an X direction along the arrays of the pixels 55, and are arranged at a predetermined pitch in a Y direction along the columns of the pixels 55. The signal lines 57 extend in the Y direction, and are arranged at a predetermined pitch in the X direction. The scan lines 56 are perpendicular with the signal lines 57. The pixels 55 are disposed at intersection points between the scan lines 56 and the signal lines 57. Note that N and M are integers equal to or more than 2, for example, are approximately 2,000. Also, the pixels 55 can be arranged in a honeycomb arrangement in place of a square arrangement of the present embodiment.

Each of the pixels 55 includes a photoconductor 58 for photoelectric conversion and a thin film transistor 59 or TFT. The photoconductor 58 generates charge (electron-hole pair) upon receiving visible light and stores the charge. The thin film transistor 59 is a switching element. The photoconductor 58 includes semiconductor layers for generating the charge, and upper and lower electrodes disposed on the semiconductor layers. An example of the semiconductor layers is a PIN type (p-intrinsic-n), in which an N layer is formed on the side of the upper electrode, and a P layer is formed on the side of the lower electrode. The thin film transistor 59 has a gate connected with the scan lines 56, a source connected with the signal lines 57, and a drain connected with the lower electrode of the photoconductor 58. Also, it is possible to use a sensor panel of CMOS type (Complementary Metal Oxide Semiconductor) instead of the TFT type.

A bias line (not shown) is connected to the upper electrode of the photoconductor 58. A bias voltage of a positive value is applied to the upper electrode of the photoconductor 58 by use of the bias line. As an electric field is created in the semiconductor layers by application of the positive bias voltage, the electron in the electron-hole pair generated in the semiconductor layers by photoelectric conversion is moved to the upper electrode and absorbed in the bias line.

The hole in the electron-hole pair is moved to the lower electrode and collected as charge.

The circuit board 41 includes a scanning device 65, a signal processor 66, a memory 67, and a controller 68 or regulation unit.

The scanning device 65 is connected to respective ends of the scan lines 56, and generates a gate pulse G(K) for driving the thin film transistor 59, where K is an integer from 1 to N. The controller 68 drives the thin film transistor 59 by use of the scanning device 65, and causes the sensor panel 40 to operate for pixel reset, storing and image readout. In the pixel reset, dark current is read out from the pixels 55 and reset. In the storing, the charge according to the dose of the X-rays is stored in the pixels 55. In the image readout, charge is read out from the pixels 55.

In the pixel reset and image readout, the scanning device 65 supplies the scan lines 56 with the gate pulse G(K), so that the thin film transistors 59 connected with the scan lines 56 are turned on successively one array after another. In the storing, no gate pulse G(K) is output by the scanning device 65. The thin film transistors 59 are turned off.

The signal processor 66 reads out charge from the pixels 55 and converts this into a digital image signal, which is output to the memory 67 as a radiation image. The memory 67 has capacity for storing at least one frame of the radiation image.

The controller 68 receives various data from the console device 17 as input by use of the first radio communication unit 22, and performs control according to the various data. For example, the controller 68 receives an exposure condition, and changes a processing condition in the signal processor 66 according to the exposure condition. The controller 68 registers a console ID in the first radio communication unit 22 as a recipient of the radiation image.

Plural monitor sensors 69 for radiation or X-rays are disposed in the photosensitive plate 45 for detecting a start of exposure (irradiation) of X-rays. The monitor sensors 69 are arranged in a discrete manner within the entire surface of the photosensitive plate 45.

The monitor sensors 69 are a structure of partial use of the pixels 55. The monitor sensors 69 include the photoconductor 58 in the same manner as the pixels 55, but do not have the thin film transistor 59. The photoconductor 58 in the monitor sensors 69 is directly connected to the signal lines 57. Charge generated by the photoconductor 58 in the monitor sensors 69 is drawn to the signal lines 57 irrespective of a turn-on or turn-off state of the thin film transistor 59.

The charge generated by the photoconductor 58 in the monitor sensors 69 is converted by the signal processor 66 into an image signal and written to the memory 67, in the same manner as the charge generated by the photoconductor 58 in the pixels 55. Note that a term of a dose signal is used herein to express the image signal according to the charge generated by the photoconductor 58 in the monitor sensors 69.

The dose signal is read out repeatedly at a predetermined interval. The dose signal obtained by the readout of one event corresponds to a dose of incident X-rays per unit time. The dose per unit time increases gradually upon a start of exposure of X-rays, so that a value of the dose signal increases.

The controller 68 reads out the dose signal from the memory 67 at each time that the dose signal is written to the memory 67, and compares a value of the dose signal with the value of a predetermined detection threshold for detecting a start of the exposure. The controller 68 judges that the exposure of X-rays is started upon reach of the dose signal to the detection threshold. Thus, the start of the exposure can be detected in the electronic cassette 16 without receiving a sync signal expressing the start of the exposure from the source control unit 14.

As the dose signal can be read out even during the storing of the sensor panel 40, it is possible to detect an end of the exposure of X-rays in the controller 68 by comparison of the dose signal with a predetermined detection threshold for the end of the exposure.

Figure 8:
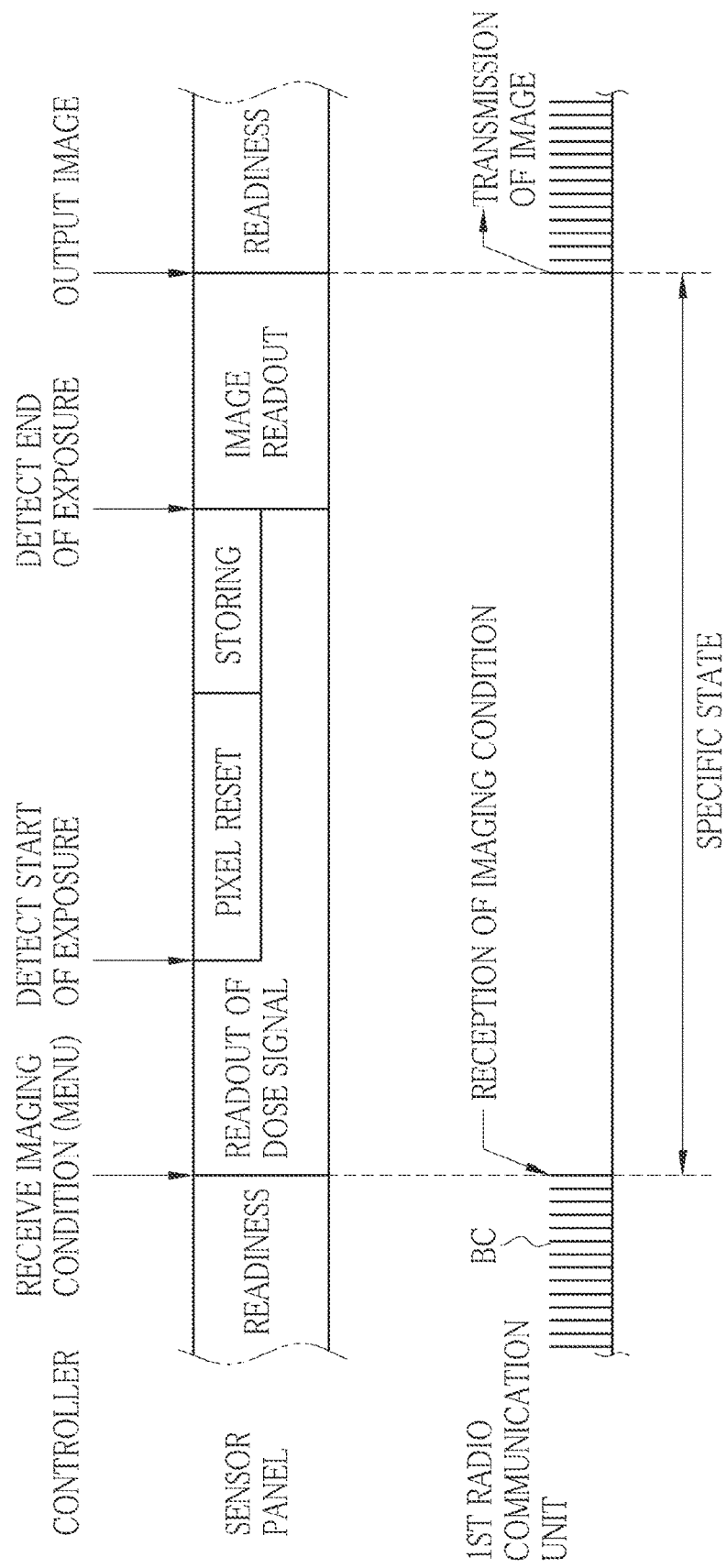
FIG. 8 is a timing chart illustrating a flow of a radiographic imaging apparatus.

In an upper portion of FIG. 8, the controller 68 upon receiving the various data including the imaging condition (menu for the object) from the console device 17 causes the sensor panel 40 to start reading out the dose signal. Before the controller 68 receives the various data, the sensor panel 40 is in a state of readiness in which only the bias voltage is applied to the upper electrode of the photoconductor 58. It is judged that the exposure of X-rays is started upon reach of the dose signal to the detection threshold in the course of monitoring.

Upon detecting the start of the exposure (irradiation), the controller 68 causes the sensor panel 40 to perform the pixel reset, and then perform the storing. Even after the start of the storing, the controller 68 causes the sensor panel 40 to continue reading out the dose signal. The controller 68 detects an end of the exposure in case the dose signal becomes equal to or less than the detection threshold. The controller 68 completes the storing upon detecting the end of the exposure. The controller 68 causes the sensor panel 40 to perform the image readout. After the image readout, the sensor panel 40 returns to the state of the readiness.

Immediately after completing the image readout, the controller 68 outputs the radiation image read from the memory 67 to the first radio communication unit 22. The first radio communication unit 22 transmits the radiation image to the second radio communication unit 23.

The controller 68 operates as a regulation unit for regulating beaconing of the beacon BC from the first radio communication unit 22 in a predetermined specific state included in the plural operational states of the electronic cassette 16. To be precise, the controller 68 turns off the beacon BC from the first radio communication unit 22 as illustrated in a lower portion of FIG. 8, namely, in a period from reception of various data with the imaging condition in the first radio communication unit 22 and start of the readout of the dose signal of the sensor panel 40 by receiving the various data from the first radio communication unit 22, until termination of the image readout in the sensor panel 40 and start of the transmission of the radiation image in the first radio communication unit 22. In the embodiment, the specific state is a state in a period from a start of the readout of the dose signal in the sensor panel 40 until termination of the image readout in the sensor panel 40.

The controller 68 does not regulate beaconing of the beacon BC in a state different from the specific state, for example, before receiving various data including the imaging condition (menu for the object), and after completing the image readout of the sensor panel 40. Thus, the first radio communication unit 22 transmits the beacon BC at a predetermined beacon interval before receiving the various data and after completing the image readout of the sensor panel 40. Therefore, the first radio communication unit 22 can receive the various data at any suitable time point. The first radio communication unit 22 can immediately transmit the radiation image after completing the image readout.

Figure 9:
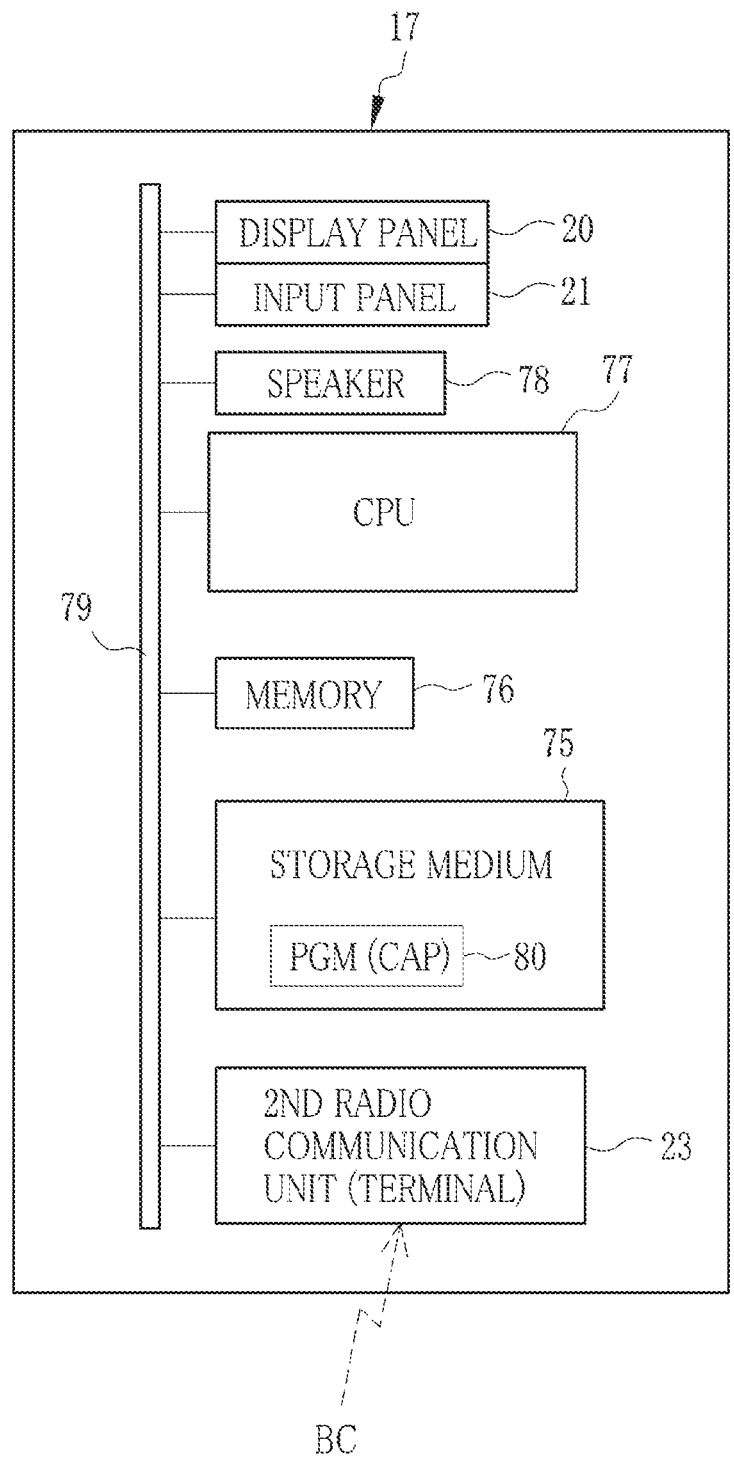
FIG. 9 is a block diagram schematically illustrating a computer for a console device.

In FIG. 9, a computer constituting the console device 17 includes the display panel 20, the input panel 21 and the second radio communication unit 23 (terminal) described above, and also a storage medium 75 or storage device, a memory 76, a CPU 77 (central processing unit) and a speaker 78 as alert indicator. A data bus 79 connects those elements with one another.

The storage medium 75 is a hard disk drive incorporated in a computer constituting the console device 17. Various programs and data are stored in the storage medium 75, including control programs such as an operating system (OS), an application program 80 such as a console application program (CAP), and display data for control pages of display associated with those programs. The application program 80 is a program for functioning the computer as the console device 17.

The memory 76 is a working memory with which the CPU 77 performs tasks. The CPU 77 loads the memory 76 with the programs read from the storage medium 75, and controls various elements in the computer by processing according to the programs.

Figure 10:
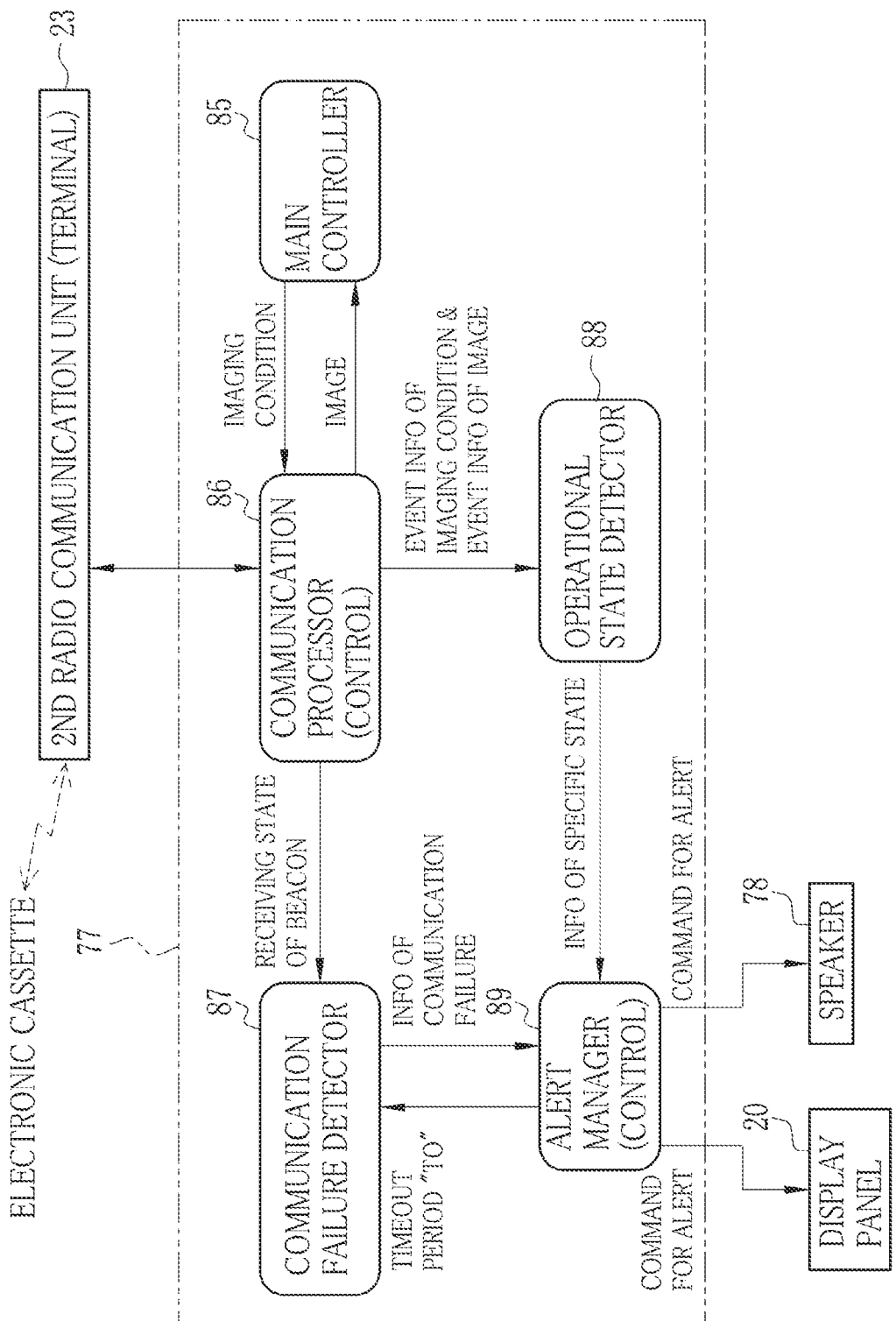
FIG. 10 is a block diagram schematically illustrating a CPU.

In FIG. 10, a main controller 85, a communication processor 86 (communication control unit), a communication failure detector 87, an operational state detector 88, and an alert manager 89 or alert controller become active in the CPU 77 in case the application program 80 is run by use of the memory 76.

The main controller 85 controls various functions of the applications provided by the application program 80. The main controller 85, upon receiving a command signal of the imaging condition (menu for the object) input by the operator with the input panel 21, transfers various data to the communication processor 86 inclusive of the imaging condition from the operator. The main controller 85 drives the display panel 20 to display the radiation image received by the second radio communication unit 23.

The communication processor 86 processes the radio communication in the second radio communication unit 23. Various data transferred from the main controller 85 are output by the communication processor 86 to the second radio communication unit 23. Also, the communication processor 86 acquires a radiation image received in the second radio communication unit 23, and inputs the radiation image to the main controller 85.

The communication processor 86 outputs event information of (transmission of) the imaging condition (menu for the object) to the operational state detector 88 to notify that the various data including the imaging condition are wirelessly transmitted by the second radio communication unit 23 upon outputting the data with the imaging condition to the second radio communication unit 23. Also, the communication processor 86 outputs event information of (the acquisition of) the radiation image to the operational state detector 88 upon acquiring the radiation image from the second radio communication unit 23.

The communication processor 86 checks a receiving state of receiving the beacon BC in the second radio communication unit 23, and outputs information of the receiving state to the communication failure detector 87. The communication failure detector 87 checks occurrence of a communication failure in the radio communication between the radio communication units 22 and 23 according to the receiving state of the beacon BC from the communication processor 86. Assuming that the occurrence is judged, then the communication failure detector 87 outputs information of the occurrence of the communication failure to the alert manager 89.

The operational state detector 88 checks whether an operational state of the electronic cassette 16 is a specific state. In the embodiment, a period of the specific state is defined from the reception of various data including the imaging condition (menu for the object) in the first radio communication unit 22 and start of readout of the dose signal in the sensor panel 40 until completion of the image readout in the sensor panel 40 and start of transmission of the radiation image in the first radio communication unit 22. The operational state detector 88 judges that the operational state of the electronic cassette 16 is the specific state in a period from receiving the information of the imaging condition from the communication processor 86 until receiving event information of (the acquisition of) the radiation image. Assuming that the electronic cassette 16 is not in the specific state, the operational state detector 88 judges that the electronic cassette 16 is in a non-specific state.

Assuming that the non-specific state is detected, the operational state detector 88 does not operate. Assuming that the specific state is detected, the operational state detector 88 outputs information of the specific state to the alert manager 89.

The alert manager 89 outputs the command signal to the display panel 20 and the speaker 78 for alert notification. The display panel 20 and the speaker 78 are turned on to generate alert notification expressing occurrence of the communication failure in response to the command signal. The display panel 20 and the speaker 78 operate as the alert indicator.

Figure 11:
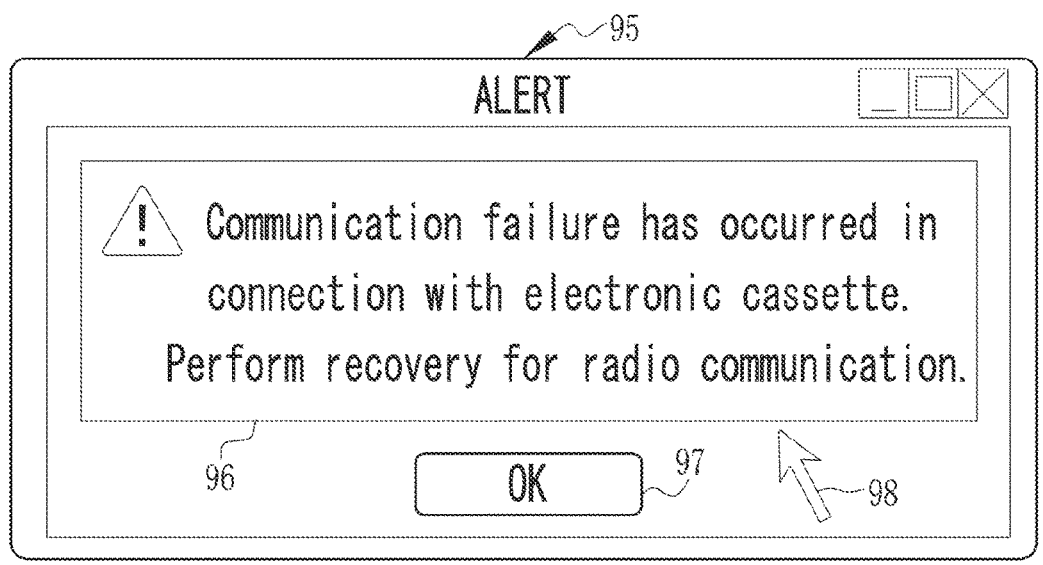
FIG. 11 is a screen view illustrating an alert notification.

In case the alert manager 89 generates the command signal, an alert notification 95 is displayed in the display panel 20 as illustrated in FIG. 11. Alert message information 96 and an OK button 97 are indicated in the alert notification 95. The alert message information 96 is information of occurrence of a communication failure in the radio communication with the electronic cassette 16, and encourages an operator to manipulate for recovery of the radio communication. A cursor 98 is indicated in the alert notification 95. The alert notification 95 remains displayed in the display panel 20 until the OK button 97 is pressed (selected) by use of the cursor 98.

In case the alert manager 89 generates a command signal, the speaker 78 emits alert sound, such as beep sound. The speaker 78 outputs the alert sound until the OK button 97 in the alert notification 95 is pressed (selected) by the cursor 98.

In case the state without receiving the beacon BC in the second radio communication unit 23 (receiving state of NG for receiving the beacon BC) is continued during the predetermined timeout period TO, then the communication failure detector 87 judges occurrence of the communication failure, and outputs information of the occurrence of the communication failure to the alert manager 89. See FIGS. 12 and 13. Data of the timeout period TO is stored in, for example, an internal memory (not shown) in the main controller 85. The alert manager 89 reads out the timeout period TO from the internal memory and registers this in the communication failure detector 87. See FIG. 10. An example of the timeout period TO is 2 seconds.

Figure 12:
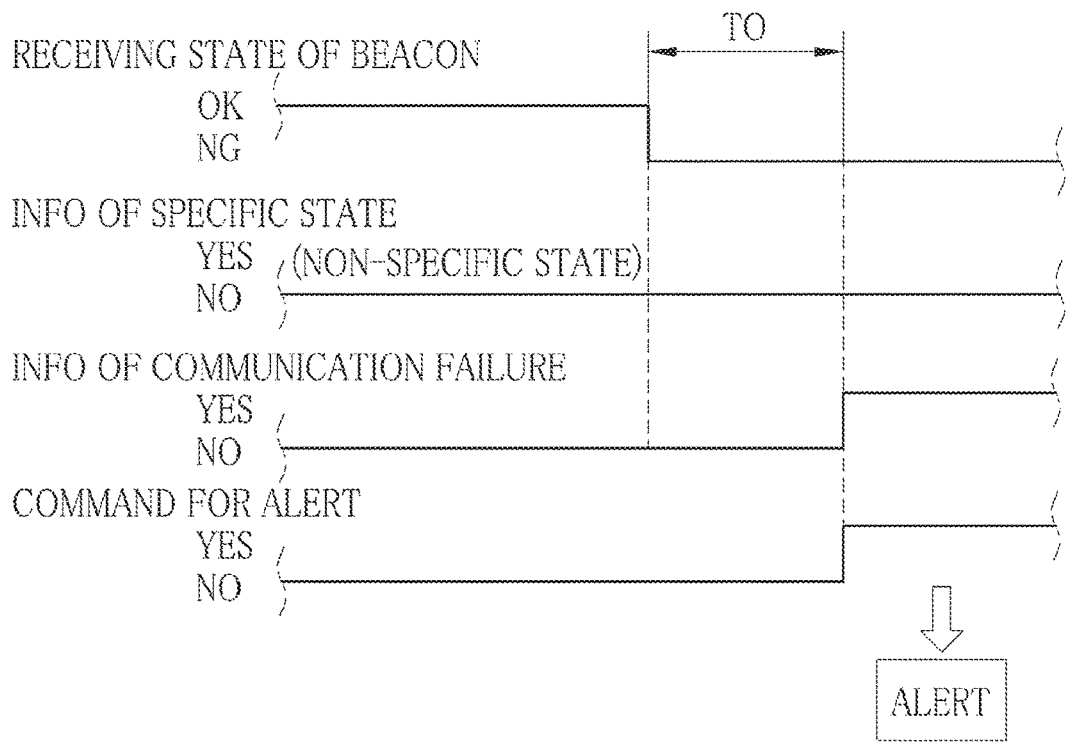
FIG. 12 is a timing chart illustrating generation of alert in a non-specific state.

In FIG. 12, a condition without the information of the specific state is illustrated. Namely, the non-specific state is detected by the operational state detector 88. In case information of occurrence of the communication failure is received from the communication failure detector 87 in the non-specific state, the alert manager 89 generates a command signal to drive the display panel 20 and the speaker 78 to generate alert notification.

Figure 13:
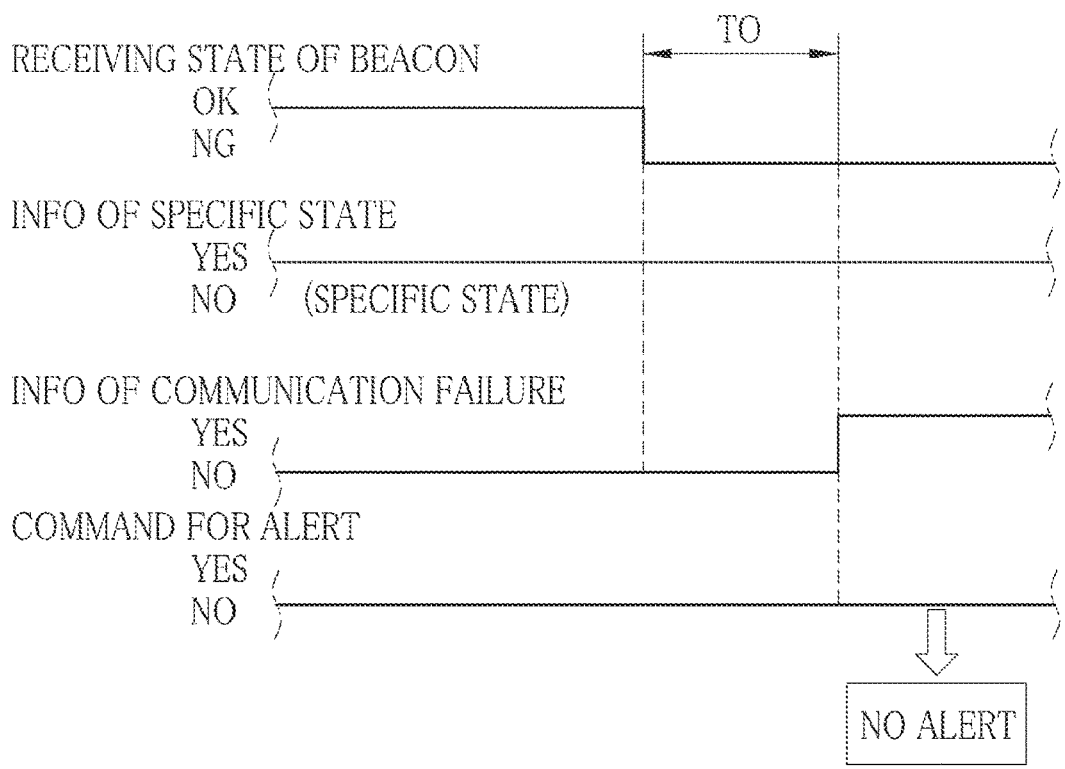
FIG. 13 is a timing chart illustrating generation of alert in a specific state.

In FIG. 13, detection of the specific state in the operational state detector 88 is illustrated (yes for transmission of information of the specific state). The alert manager 89 disables the display panel 20 and the speaker 78 from generating the alert notification during the period of the specific state. To be precise, the alert manager 89 does not output a command signal for the alert notification even upon receiving information of the communication failure from the communication failure detector 87, so that the display panel 20 and the speaker 78 do not operate.

Figure 14:
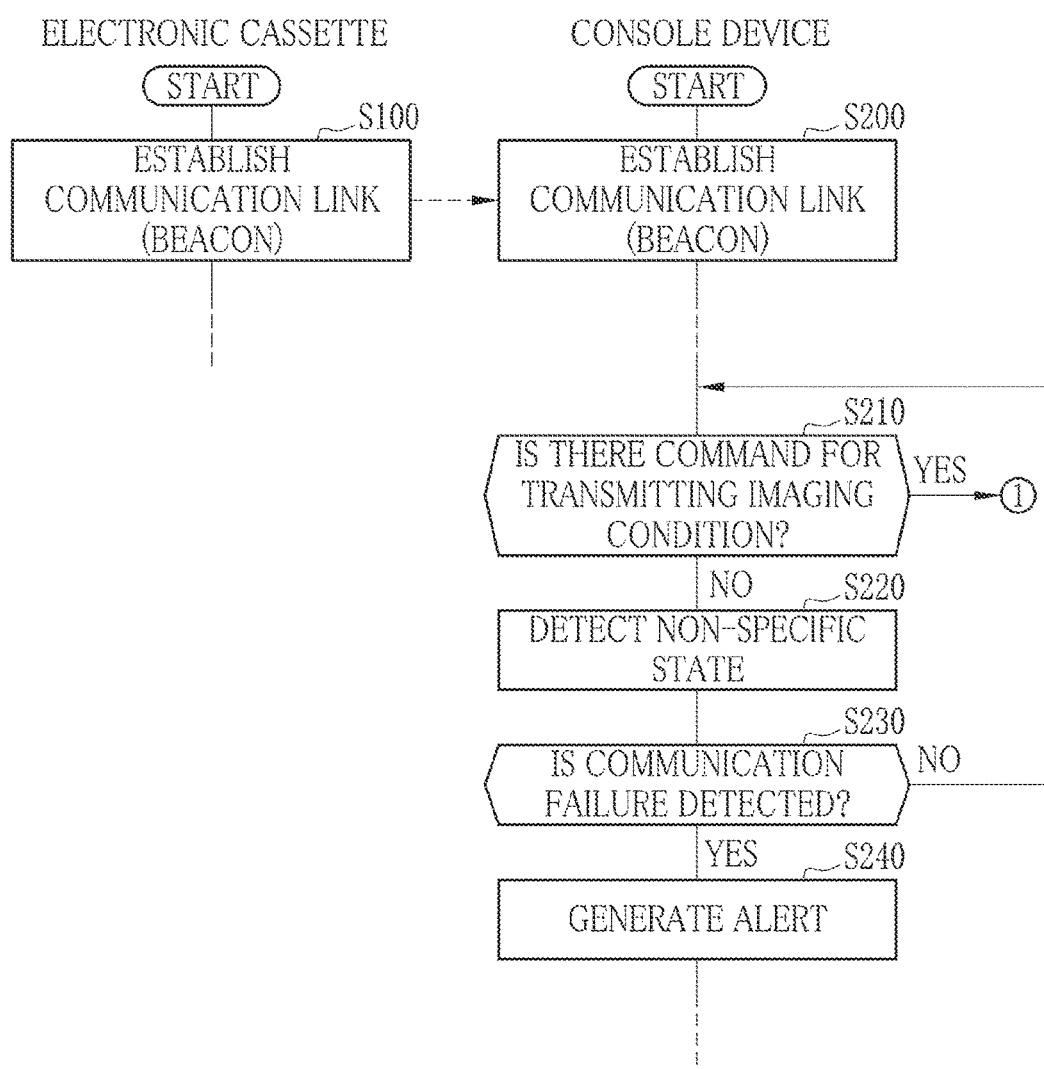
FIG. 14 is a flow chart illustrating a first flow of the electronic cassette and the console device.
Figure 15:
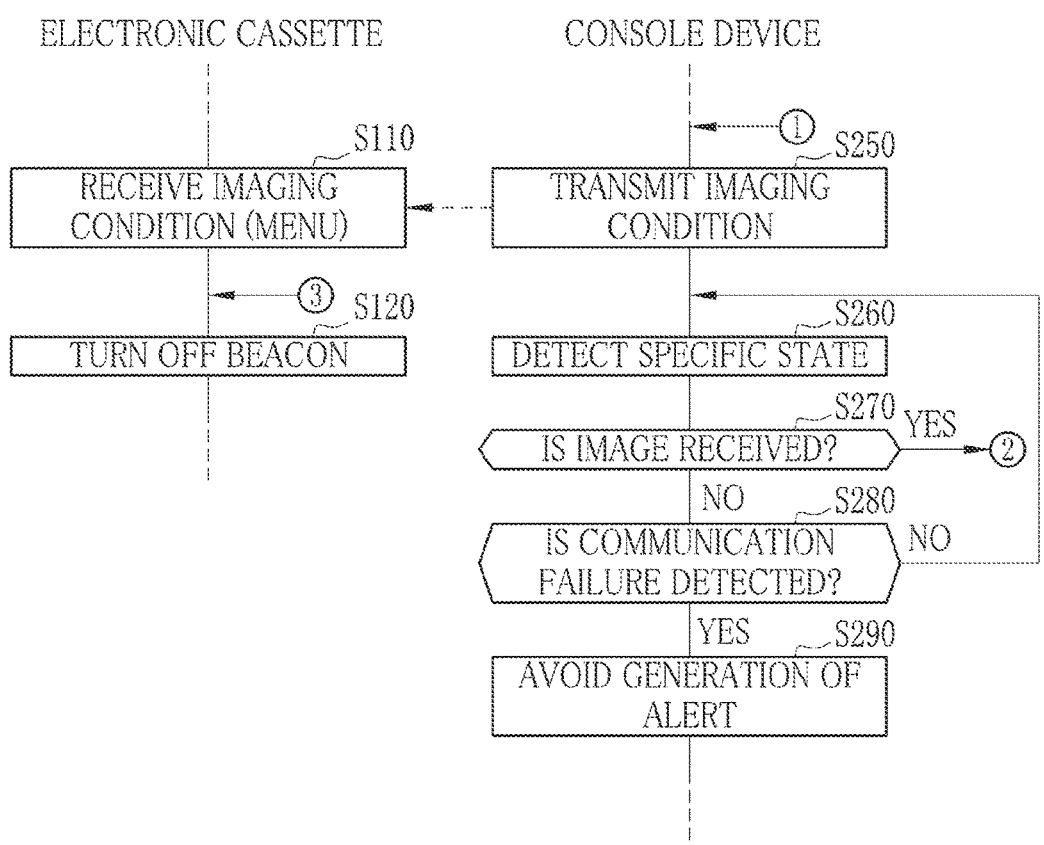
FIG. 15 is a flow chart illustrating a second flow of the electronic cassette and the console device.
Figure 16:
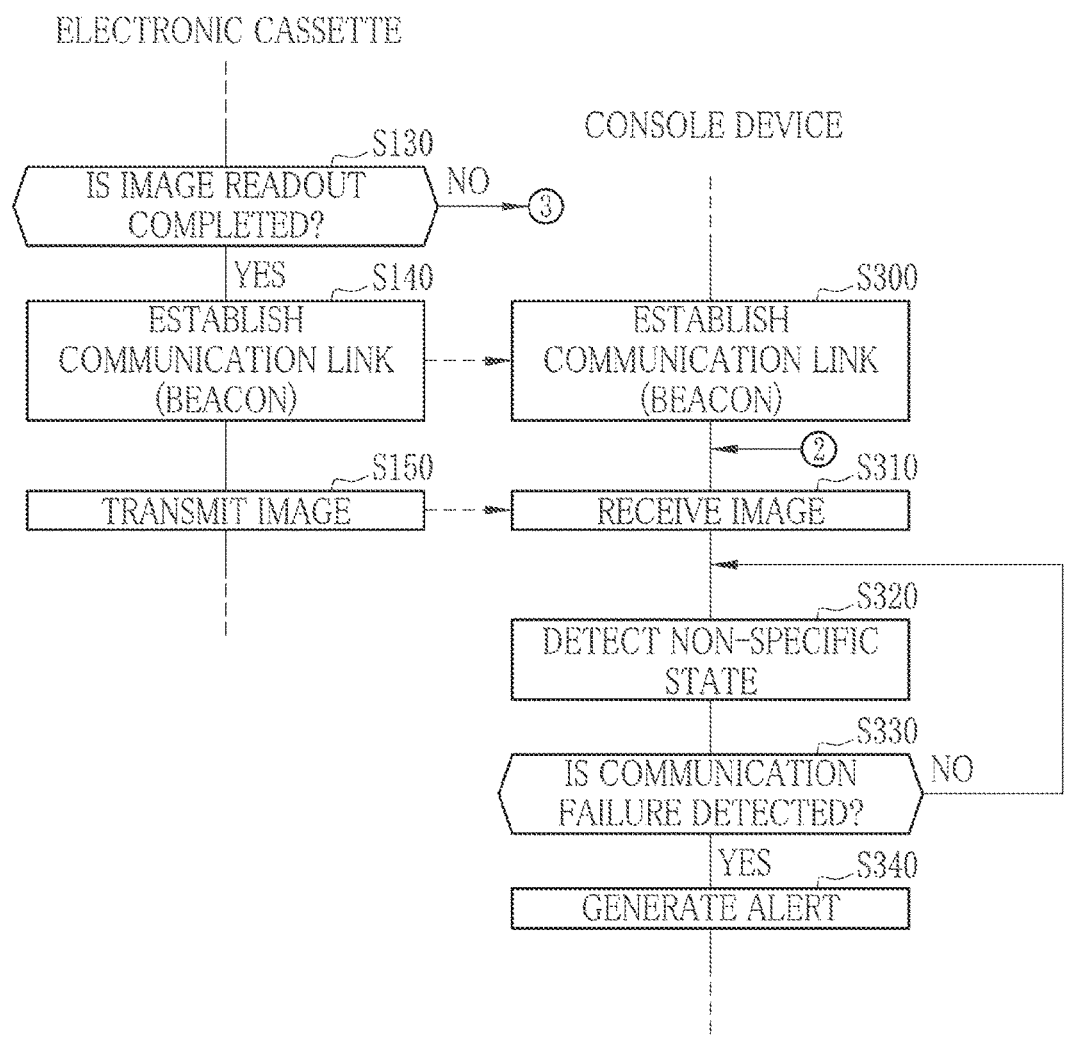
FIG. 16 is a flow chart illustrating a third flow of the electronic cassette and the console device.

The operation of the above construction is described by referring to the flow in FIGS. 14-16. At first, the first radio communication unit 22 emits the beacon BC, which is received by the second radio communication unit 23, in steps S100 and S200 of FIG. 14 to perform the connecting sequence of FIG. 3. A communication link is established between the radio communication units 22 and 23.

In the drawing, a step before receiving the event information of (transmission of) the imaging condition (menu for the object) from the communication processor 86 after confirmed entry of the imaging condition with the input panel 21 according to the operator is illustrated (no in a step S210). The operational state detector 88 detects a non-specific state of the electronic cassette 16 in a step S220.

Assuming that the communication failure detector 87 judges occurrence of the communication failure in the non-specific state (yes in a step S230), the alert manager 89 outputs a command signal for alert notification. Then the display panel 20 displays the alert notification 95. The speaker 78 emits alert sound, for example, beep sound, to generate the alert notification for informing occurrence of the communication failure in a step S240.

In case he or she inputs a command signal for transmitting the imaging condition (menu for the object) by use of the input panel 21 (yes in the step S210), the second radio communication unit 23 transmits the various data with the imaging condition to the first radio communication unit 22 as indicated in a step S250 of FIG. 15.

In the electronic cassette 16, the first radio communication unit 22 receives various data from the second radio communication unit 23 in a step S110 of FIG. 15. The controller 68 reads the data received by the first radio communication unit 22. The sensor panel 40 starts reading out a dose signal. The controller 68 causes the first radio communication unit 22 to turn off the beacon BC in a step S120. The turn-off of the beacon BC is continued while the sensor panel 40 continues the image readout (no in the step S130 in FIG. 16).

The controller 68 turns off the beacon BC in a period after the sensor panel 40 starts the readout of the dose signal until the sensor panel 40 terminates the image readout. It is possible reliably to prevent degradation of a radiation image due to occurrence of noise of the beacon BC with the radiation image. Also, power required for the beaconing can be saved.

In case the second radio communication unit 23 transmits the various data, the operational state detector 88 receives event information of (the transmission of) the imaging condition (menu for the object) from the communication processor 86. Then the operational state detector 88 judges that the operational state of the electronic cassette 16 is the specific state in a step S260. The result of the judgment of the operational state detector 88 for the specific state is continued while no radiation image is received in the second radio communication unit 23 (no in a step S270).

Assuming that the communication failure detector 87 judges occurrence of a communication failure in the specific state (yes in a step S280), there is no generation of a command signal for alert notification in the alert manager 89, in the manner different from the non-specific state. The display panel 20 does not display the alert notification 95. No sound is generated by the speaker 78, in a step S290.

After the imaging condition (menu for the object) is determined, the operator manually sets an exposure condition in the source control unit 14, the exposure condition being the same as the exposure condition corresponding to the imaging condition, or the exposure condition being obtained by finely adjusting the corresponding exposure condition according to a body size or the like of the patient body P. Then the operator positions the radiation source 13, the electronic cassette 16 and the patient body P at intended locations. Then the radiation source 13 is driven to apply X-rays to the patient P.

After receiving the imaging condition (menu for the object), the sensor panel 40 in the electronic cassette 16 reads out the dose signal. The dose signal becomes as high as the detection threshold for the start of the exposure in the course of the exposure of X-rays from the radiation source 13. The start of the exposure is detected by the controller 68, to start the storing in the sensor panel 40. Afterwards, the exposure of X-rays from the radiation source 13 is ended (turned off). The dose signal becomes lower than the detection threshold. The controller 68 detects termination of the exposure, so that the sensor panel 40 starts the image readout.

In FIG. 16, the image readout is completed (yes in a step S130). The controller 68 restarts the first radio communication unit 22 to generate the beacon BC in steps S140 and S300. The beacon BC is received by the second radio communication unit 23 to establish a communication link between the radio communication units 22 and 23. The radiation image stored in the memory 67 by the image readout is transmitted by the first radio communication unit 22 to the second radio communication unit 23 in a step S150.

In the console device 17, the second radio communication unit 23 receives the radiation image from the first radio communication unit 22 in a step S310 (yes in the steps S270 in FIG. 15). The main controller 85 drives the display panel 20 to display the radiation image for the operator to view.

In case event information of (acquisition of) the radiation image is provided by the communication processor 86 upon the reception in the second radio communication unit 23, then the operational state detector 88 judges that the operational state of the electronic cassette 16 is the non-specific state in a step S320 in the same manner as the step S220 in FIG. 14. Assuming that the communication failure detector 87 judges occurrence of the communication failure in the non-specific state (yes in a step S330), the alert manager 89 generates a command signal for alert notification in the same manner as the step S240 in FIG. 14. The display panel 20 and the speaker 78 are driven for generating alert notification in a step S340.

Therefore, the display panel 20 and the speaker 78 do not generate alert notification in relation to a communication failure even assuming that the communication failure detector 87 detects occurrence of such a communication failure while the first radio communication unit 22 turns off the beacon BC in the specific state. An operator can be free from carefully monitoring the alert notification, and does not require tasks unrelated to the radiographic imaging, such as responding to the alert notification, and checking a cause of the communication failure. It is possible to prevent the patient P from being aware of a busy condition of the operator. The radiographic imaging can be performed smoothly.

In the specific state, radio communication is not used between the electronic cassette 16 and the console device 17. Thus, a communication link between the radio communication units 22 and 23 may be interrupted. Generation of alert notification can be avoided safely without problems.

Furthermore, a change from the specific state to the non-specific state can be detected in response to the restart of the reception of the beacon BC in the second radio communication unit 23, instead of a change of the operational state in response to the event information of (the acquisition of) the radiation image.

Second Embodiment

In the first embodiment, the display panel 20 and the speaker 78 are disabled by a state without a command signal from the alert manager 89 for the purpose of avoiding the alert notification in the specific state. However, the communication failure detector 87 can be disabled for the purpose of avoiding the alert notification in the specific state instead of controlling the display panel 20 and the speaker 78.

Figure 17:
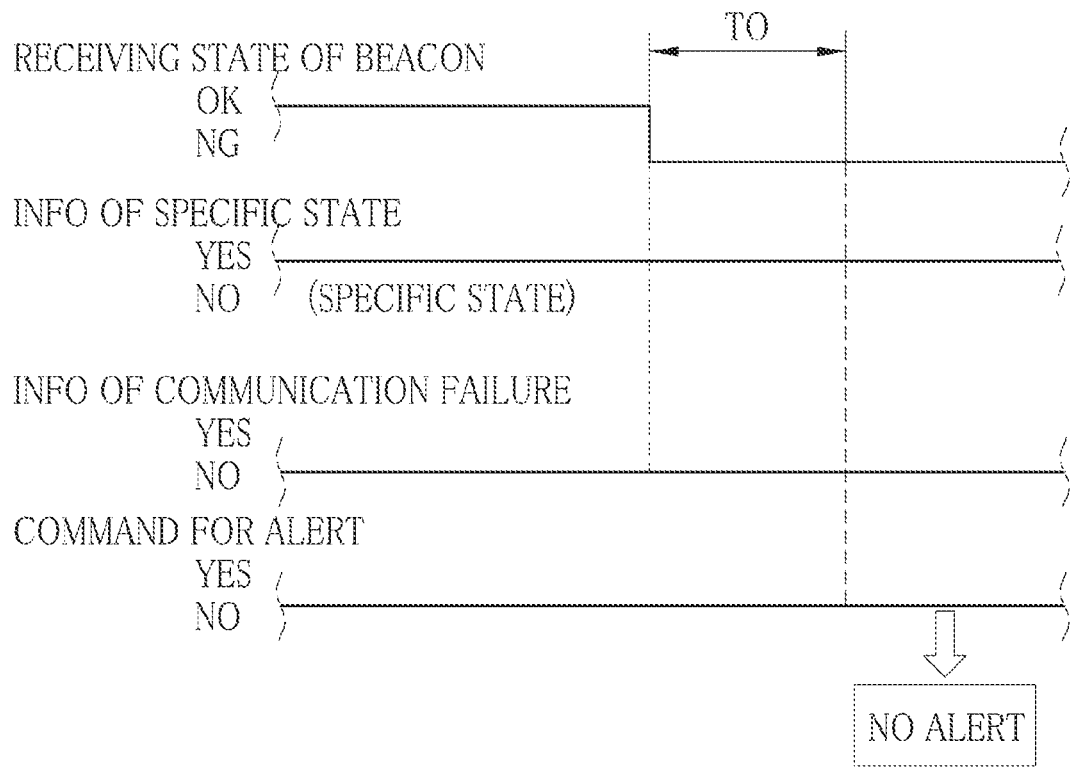
FIG. 17 is a timing chart illustrating control of alert in a second preferred radiographic imaging apparatus.

In FIG. 17, the communication failure detector 87 does not output information of occurrence of a communication failure even in case a state without receiving the beacon BC in the second radio communication unit 23 is continued in the timeout period TO in the specific state. The alert manager 89 does not output a command signal for alert notification either, because no information of occurrence of a communication failure is output. Thus, it is possible to avoid generation of alert notification in the specific state by disabling the communication failure detector 87.

Third Embodiment

A method for avoiding generation of alert notification in the specific state can be a method of elongating the timeout period TO in addition to the first embodiment of the method of turning off the display panel 20 and the speaker 78 and the second embodiment of the method of disabling the communication failure detector 87.

Figure 18:
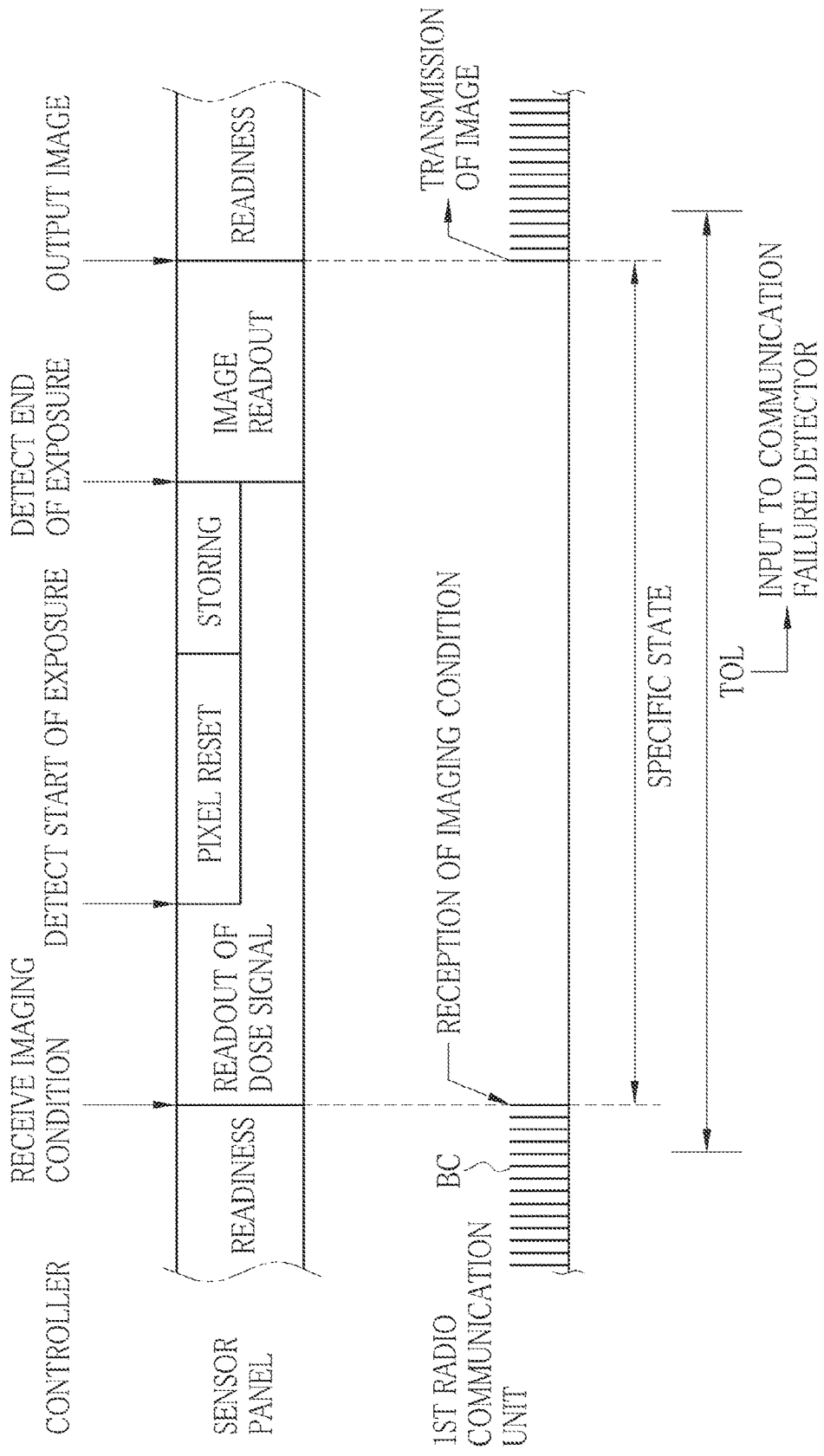
FIG. 18 is a timing chart illustrating a timeout period in a third preferred radiographic imaging apparatus.

The alert manager 89 in the specific state determines a timeout period TOL of FIG. 18 in the communication failure detector 87, as a longer value than the timeout period TO of the first embodiment (timeout period TO in the non-specific state).

The timeout period TOL is a sum of expected time and very short time for safety, the expected time being an empirically obtained period where the operational state of the electronic cassette 16 is the specific state of the first embodiment, namely, from reception of the various data in the first radio communication unit 22 inclusive of the imaging condition (transmission of the data from the second radio communication unit 23) until the start of transmitting a radiation image from the first radio communication unit 22 (reception of the radiation image in the second radio communication unit 23). The timeout period TOL is stored in, for example, an internal memory in the main controller 85 in the same manner as the timeout period TO, for example, from 180 seconds (3 minutes) to 300 seconds (5 minutes). It is possible to avoid generating the alert notification even by setting the timeout period TOL of this long value.

Fourth Embodiment

In the first embodiment, the specific state is in the period from the start of the readout of the dose signal in the sensor panel 40 until the completion of the image readout in the sensor panel 40. However, a specific state can be defined in a state of a period of performing the image readout in the sensor panel 40.

Figure 19:
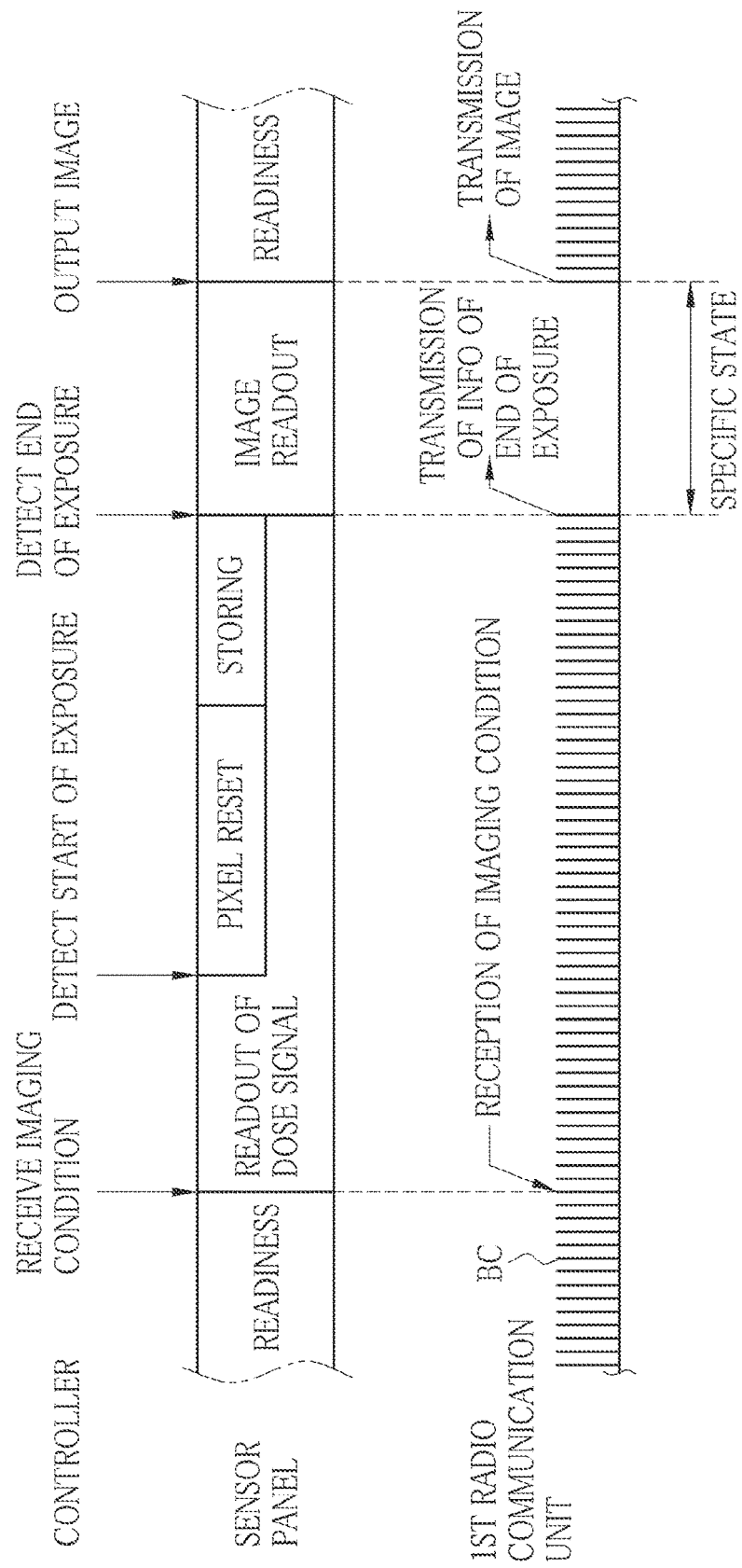
FIG. 19 is a timing chart illustrating a flow of a fourth preferred radiographic imaging apparatus.

In FIG. 19, the controller 68 causes the first radio communication unit 22 to turn off the beacon BC during the image readout, namely, in a period from detection of an end (completion) of exposure of X-rays upon decrease of the dose signal under the detection threshold of the end, until the completion of the image readout in the sensor panel 40 to start transmission of the radiation image from the first radio communication unit 22.

In the first radio communication unit 22, the controller 68 transmits information of detecting the end of the exposure to the second radio communication unit 23 before turning off the beacon BC in the controller 68. The second radio communication unit 23 receives the information of detecting the end of the exposure.

Figure 20:
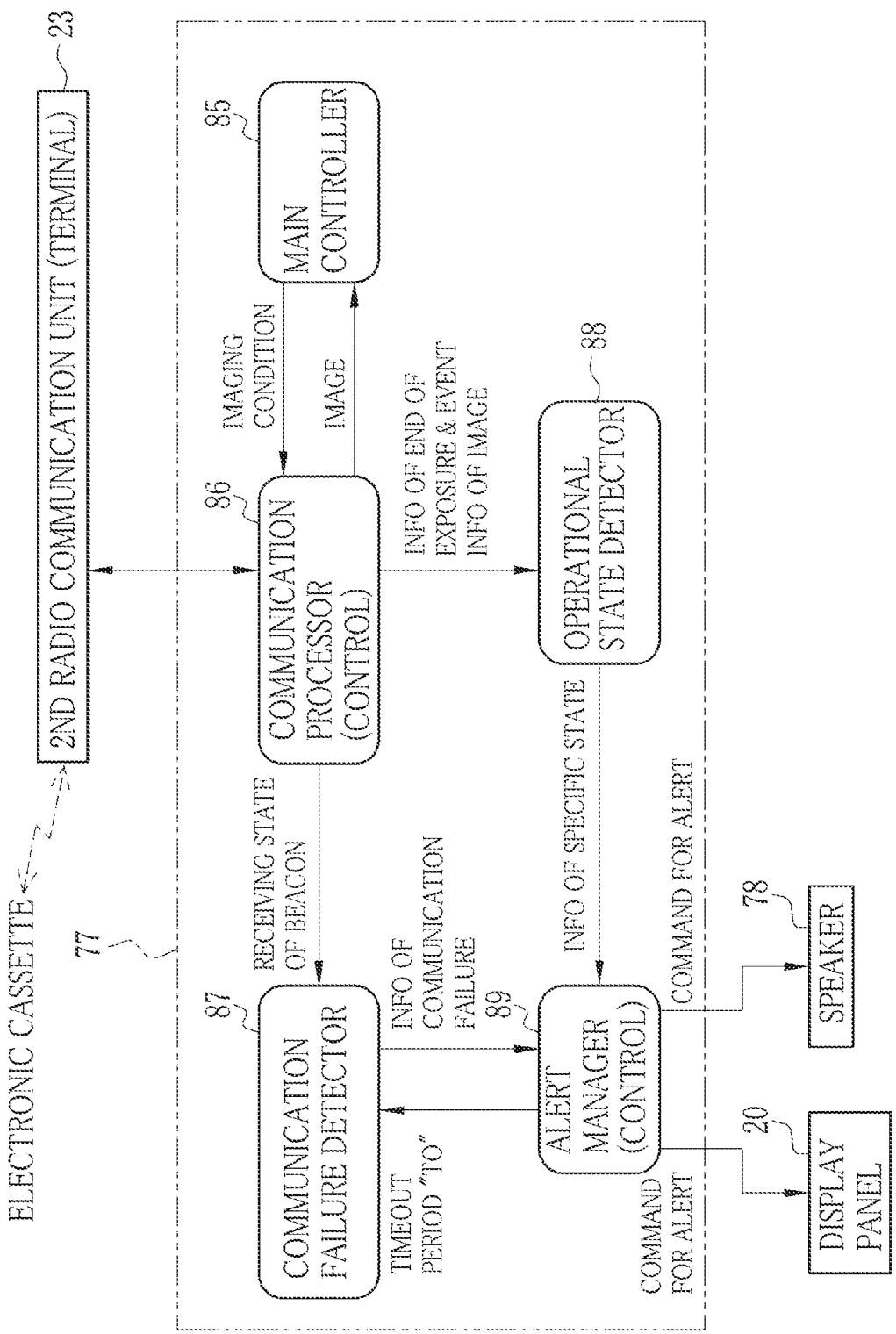
FIG. 20 is a block diagram schematically illustrating the CPU.

In FIG. 20, the communication processor 86 in the embodiment outputs information of the end of the exposure received by the second radio communication unit 23 to the operational state detector 88, instead of outputting event information of (transmission of) the imaging condition (menu for the object) in the first embodiment. The operational state detector 88 judges that the operational state of the electronic cassette 16 is the specific state in a period during the image readout, namely, from reception of the end of the exposure from the communication processor 86 until reception of event information of (acquisition of) the radiation image. Succeeding steps after this judgment are the same as the first embodiment.

It is possible reliably to prevent degradation of the radiation image in the same manner as the first embodiment, because the beacon BC is turned off during the image readout.

Fifth Embodiment

In the first embodiment, the electronic cassette 16 is single. However, a plurality of the electronic cassettes 16 can be prepared. The console device 17 causes the display panel 20 to display a selection window in which the electronic cassettes 16 are indicated as options before determining an imaging condition (menu for the object). The operator selects a main cassette among the electronic cassettes 16 for use in radiographic imaging by use of the selection window. The second radio communication unit 23 transmits the information of the main cassette to the first radio communication unit 22 of the main cassette. See FIG. 26.

The feature of the third embodiment may be combined with the fourth embodiment. In other words, the method of elongating the timeout period TO may be used for avoiding the generation of alert notification in the structure in which the specific period is defined as a state of the period of the image readout. It is preferable that the timeout period TOL is a sum of required time for the image readout and very short time for safety.

However, time required for the image readout is different between the plural electronic cassettes 16 according to their specification, for example, the size of the sensor panel 40, the number of the pixels 55, performance of the scanning device 65 and the signal processor 66 and the like. Assuming that the timeout period TOL of an equal value is set for the electronic cassettes 16, the timeout period TOL for one of those is likely to be shorter than the required time for the image readout. The alert notification may be generated even in the specific state.

In the fifth embodiment, the timeout period TOL is varied according to the required time of the image readout of the main cassette (cassette for use) for solving the problem.

Figure 21:
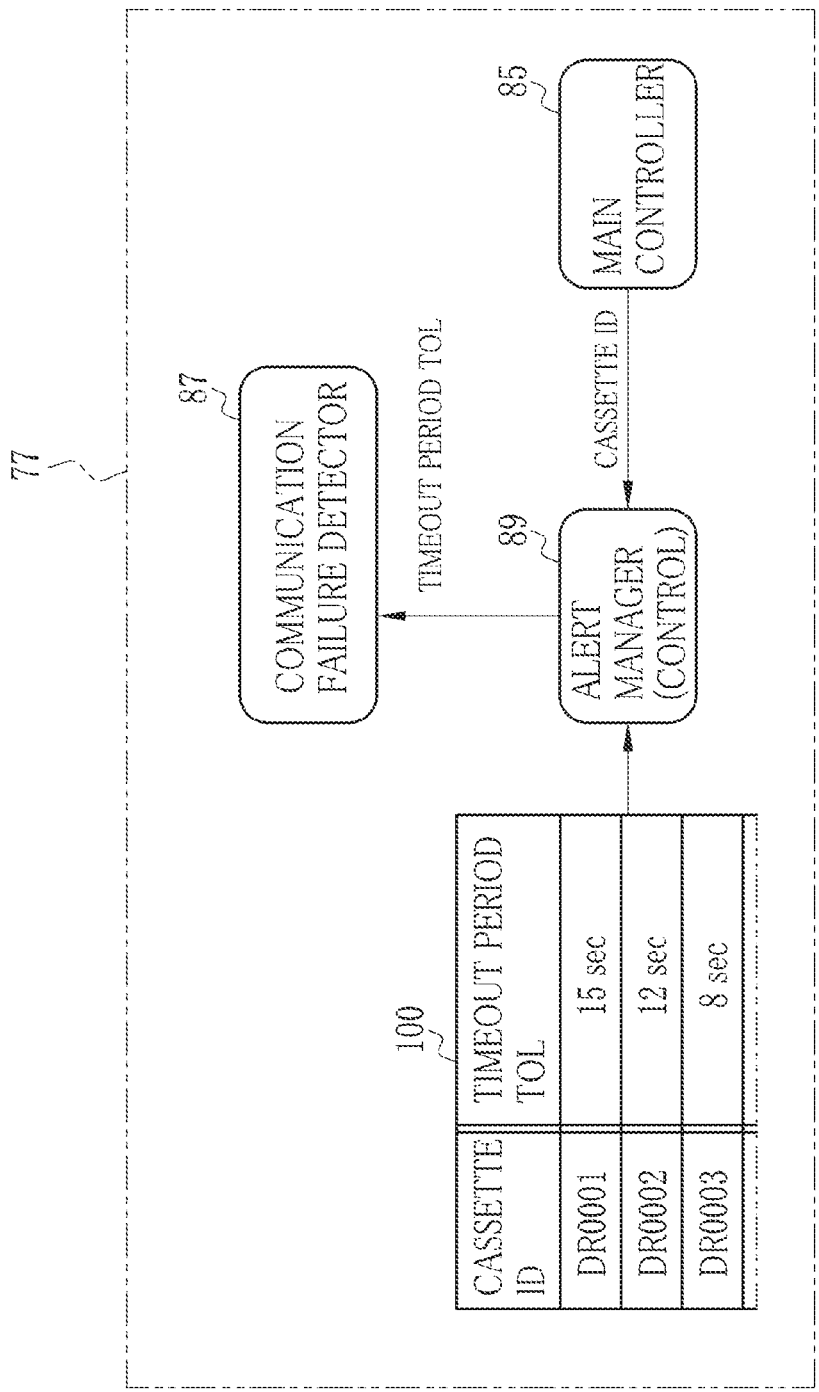
FIG. 21 is a block diagram schematically illustrating a CPU in a fifth preferred radiographic imaging apparatus.

To be precise, the main controller 85 transfers the cassette ID of the main cassette (cassette for use) selected in the selection window to the alert manager 89 as illustrated in FIG. 21.

A time list 100 is a list in which the timeout period TOL of each cassette ID is registered. The alert manager 89 reads out the timeout period TOL from the time list 100 in association with the cassette ID received from the main controller 85, and registers the timeout period TOL being read out to the communication failure detector 87. The time list 100 is stored in, for example, an internal memory in the main controller 85.

Specifically, in the time list 100, stored values of the timeout periods TOL for the plural electronic cassettes are so determined as to be high according to length of required time for image readout in the electronic cassettes.

Thus, the timeout period TOL suitable for the main cassette can be determined by changing the timeout period TOL according to the required time for the image readout. It is possible to prevent determination of the timeout period TOL shorter than the required time for the image readout, and prevent generation of the alert notification even in the specific state.

In FIG. 21, the second radio communication unit 23, the communication processor 86 and the operational state detector 88 are not illustrated. The communication processor 86 receives the cassette ID of the main cassette (cassette for use) from the main controller 85, and outputs the cassette ID to the second radio communication unit 23 in FIG. 27. Thus, the second radio communication unit 23 transmits information of the main cassette to the first radio communication unit 22 of the main cassette.

Sixth Embodiment

The electronic cassette 16 is operable for transition to a sleep state, in which only partial circuit devices in the electronic cassette 16 are powered. Also, the operational state of the electronic cassette 16 in the sleep state is defined as a specific state.

Figure 22:
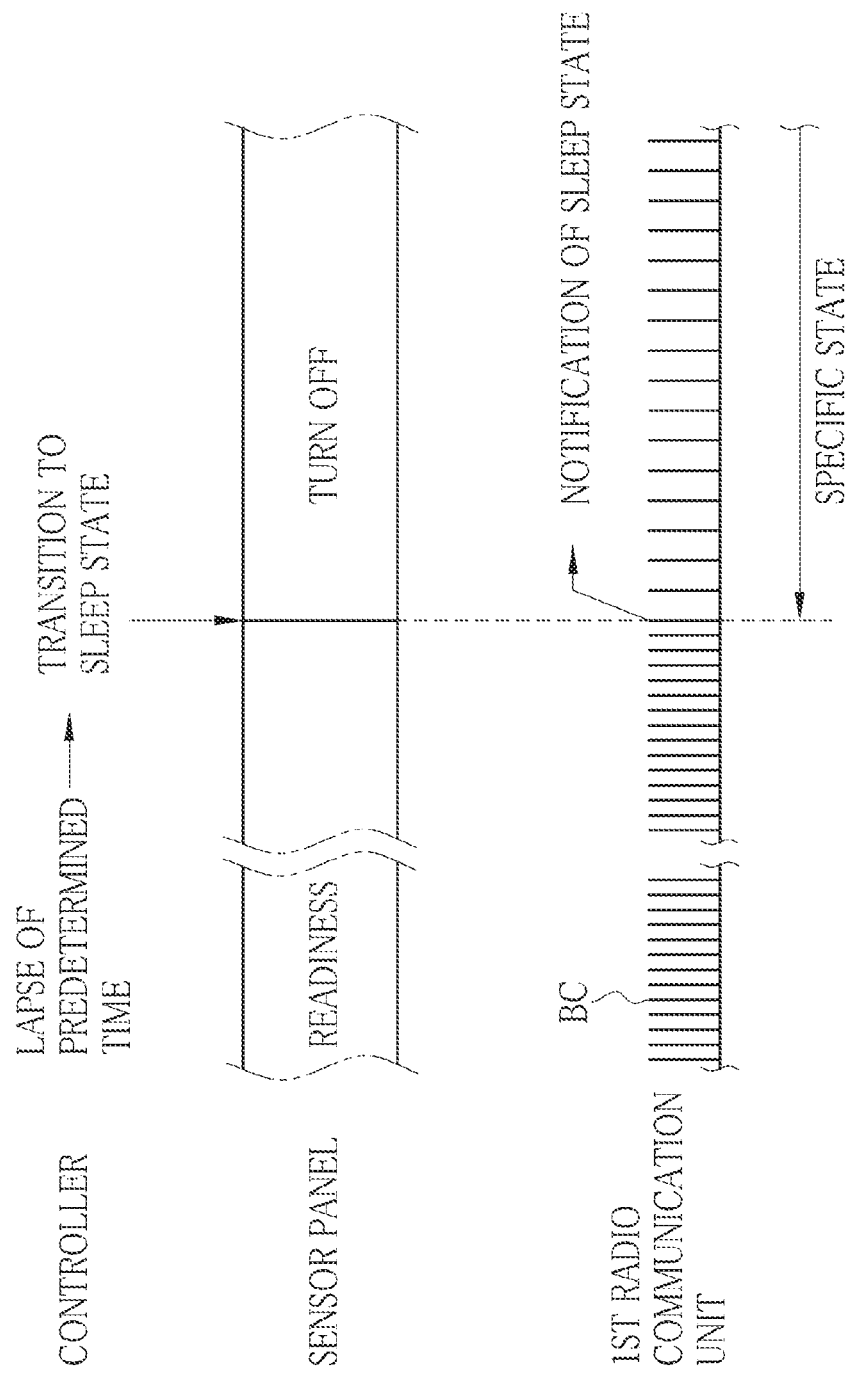
FIG. 22 is a timing chart illustrating a flow of a sixth preferred radiographic imaging apparatus.

Let the sensor panel 40 operate in the state of readiness. Assuming that the first radio communication unit 22 does not receive various data including the imaging condition (menu for the object) even upon a lapse of a predetermined time, the controller 68 causes the various elements in the electronic cassette 16 to transit to the sleep state. See FIG. 22.

In the sleep state, application of the bias voltage to the upper electrode of the photoconductor 58 is turned off for the purpose of minimizing power for use. The sensor panel 40 is turned off. Power is supplied to the first radio communication unit 22 and the controller 68 but not to the scanning device 65 and the signal processor 66. The sleep state is terminated in case the first radio communication unit 22 receives information of the main cassette, or receives various data including the imaging condition (menu for the object).

The controller 68 performs the transition to the sleep state, and also sets the beacon interval of the beacon BC in the first radio communication unit 22 larger than the beacon interval in the non-specific state. For example, the beacon interval is changed from approximately 100 msec to approximately 200 msec.

Upon occurrence of the transition to the sleep state according to the controller 68, the first radio communication unit 22 transmits information of the transition to the sleep state to the second radio communication unit 23. The second radio communication unit 23 receives the information of the transition to the sleep state.

Figure 23:
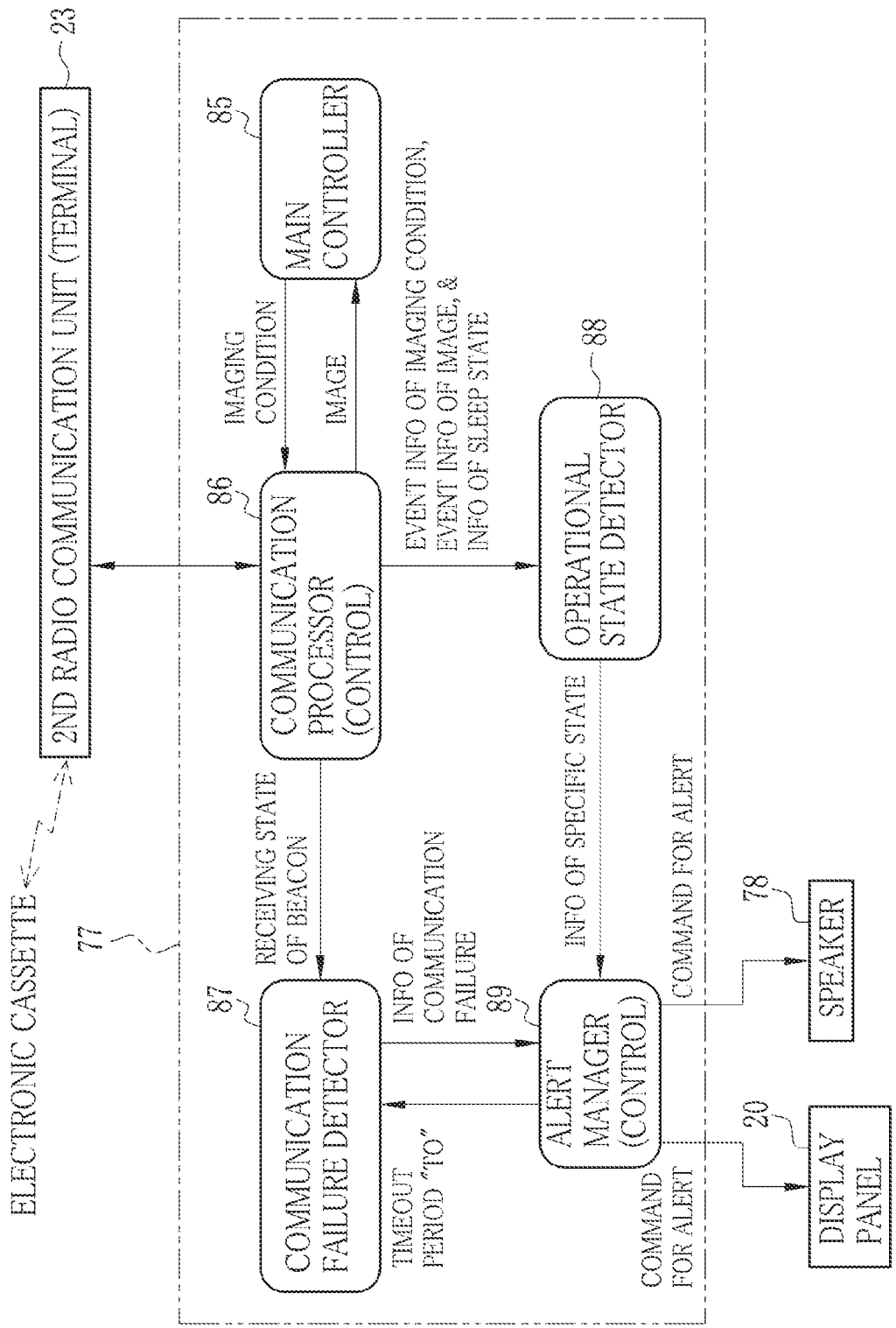
FIG. 23 is a block diagram schematically illustrating the CPU.

In FIG. 23, the communication processor 86 in the embodiment outputs the information of the transition to the sleep state from the second radio communication unit 23 to the operational state detector 88 in addition to the event information of (transmission of) the imaging condition and event information of (acquisition of) the radiation image. The operational state detector 88 judges that the operational state of the electronic cassette 16 is the specific state in a period from receiving the information of the transition to the sleep state from the communication processor 86 until receiving the event information of the radiation image. Succeeding steps after the judgment are the same as those of the first embodiment.

In conclusion, the power for use in the sleep state can be saved remarkably by setting the beacon interval of the beacon BC in the sleep state longer than the beacon interval in the non-specific state. The beacon BC continues being generated even with the increase in the beacon interval. A communication link with the console device 17 can be continuously established. The various data including the imaging condition (menu for the object) and information of the main cassette can be received by the first radio communication unit 22 at a suitable time point.

Seventh Embodiment

In the first embodiment, the radiation generator 11 is the installed type. However, the invention is not limited. Radiographic imaging can be mobile imaging, in which a radiation generator is carried for imaging in each of patient rooms.

Figure 24:
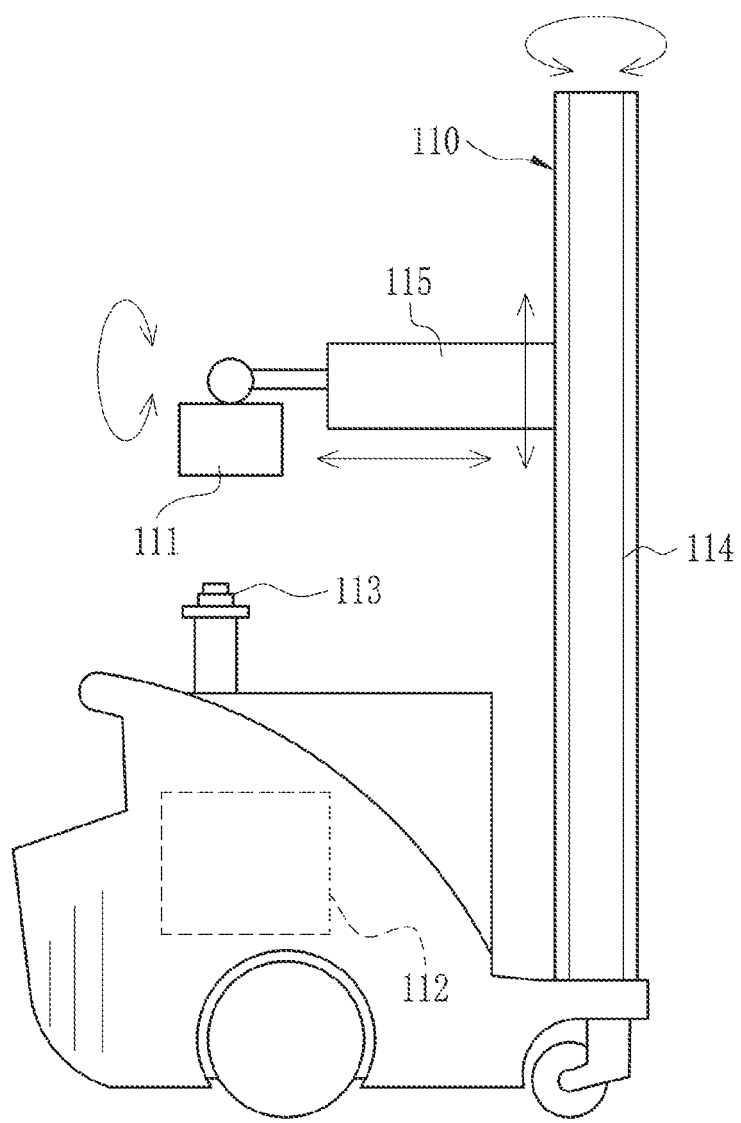
FIG. 24 is a side elevation illustrating a medical cart.
Figure 25:
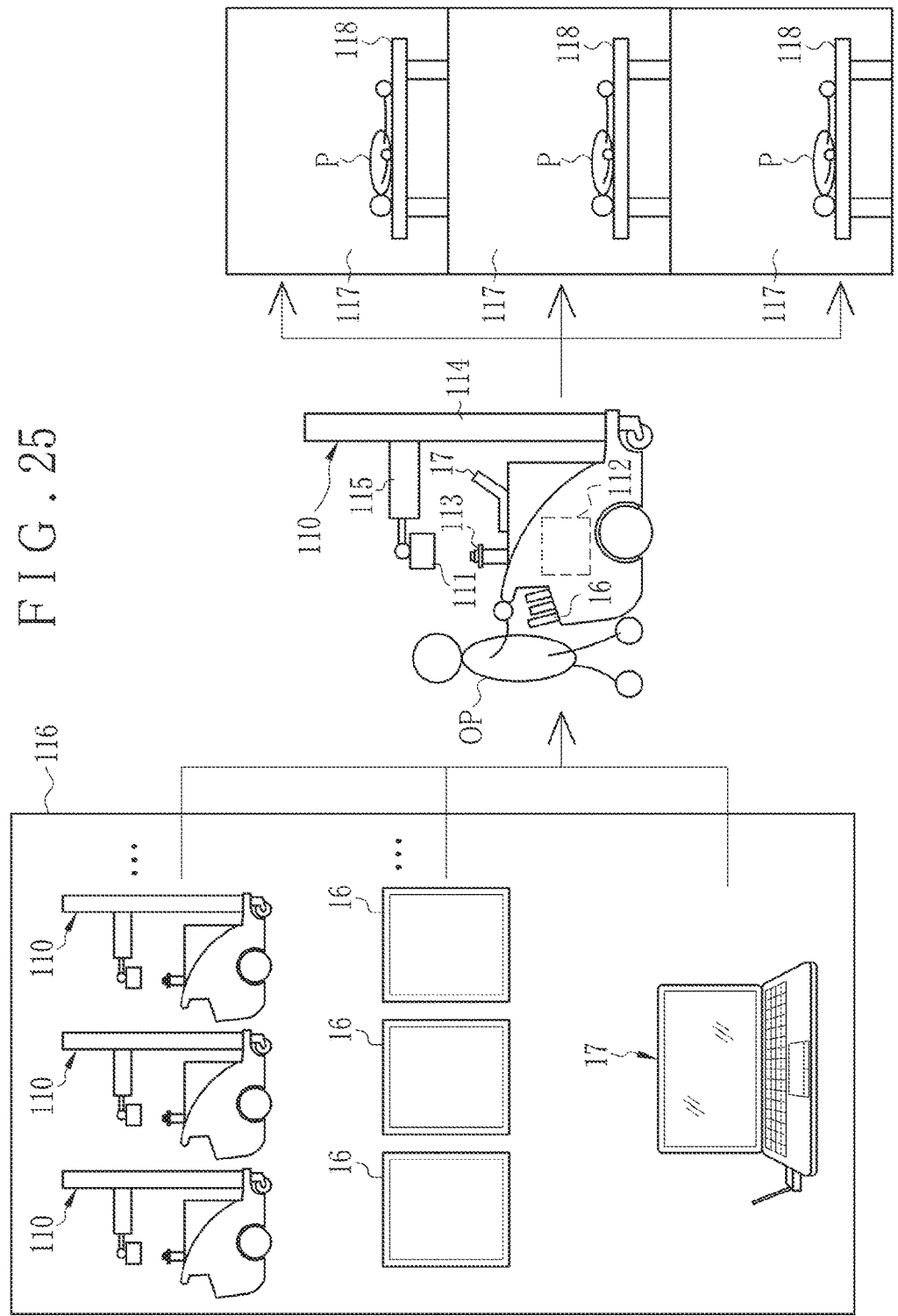
FIG. 25 is a side elevation illustrating mobile imaging.

In FIGS. 24 and 25, a medical cart 110 is used for mobile imaging in place of the radiation generator 11. The medical cart 110 has a mobile device including a housing, and includes a radiation source 111, a source control unit 112 and a radiation switch 113 disposed in the housing. The structures of the radiation source 13, the source control unit 14 and the radiation switch 15 in the first embodiment are repeated for the radiation source 111, the source control unit 112 and the radiation switch 113.

The medical cart 110 has a support column 114 and a holder arm 115. The support column 114 extends vertically. The holder arm 115 is disposed on the support column 114 and extends horizontally. The radiation source 111 is disposed at one end of the holder arm 115. The support column 114 is rotatable about an axis extending vertically. The holder arm 115 and the radiation source 111 are rotated by rotation of the support column 114. The holder arm 115 is extendable from the support column 114 and movable up and down. The radiation source 111 is rotatable on the holder arm 115. A position and direction of the radiation source 111 are adjusted by rotation of the support column 114, extension and movement of the holder arm 115 and rotation of the radiation source 111 itself. Lock mechanisms (not shown) are disposed on the support column 114 and the holder arm 115, to lock the support column 114, the holder arm 115 and the radiation source 111 without incidental shift while the medical cart 110 is moved.

The radiology department in the hospital facility includes a storage room 116 or preparation room, where the medical cart 110 is placed while not used. An operator OP or doctor or radiologist (radiology technician) moves out the medical cart 110 from the storage room 116, for positioning in a patient room 117. A patient P is disposed in each of the patient rooms 117 on a bed 118. He or she is bedridden and cannot walk to an examination room.

A plurality of the electronic cassettes 16 are disposed in the storage room 116. For the mobile imaging, the electronic cassette 16 is placed in the medical cart 110 and carried from the storage room 116. Also, the console device 17 is placed in the medical cart 110 and carried from the storage room 116 together with the electronic cassette 16.

A data item of necessity or unnecessity of the mobile imaging is included in the information of the imaging request in addition to the data items of FIG. 4. For the mobile imaging, the operator OP selects the main cassette in the storage room 116 for the imaging request of which the mobile imaging is necessary. As has been described in relation to the fifth embodiment, the second radio communication unit 23 transmits information of the main cassette to the first radio communication unit 22 of the main cassette.

After selecting the main cassette (cassette for use) for imaging, the main cassette and the console device 17 are placed by the operator OP in the medical cart 110. He or she moves from the storage room 116 to the patient room 117 together with the medical cart 110. The operator OP upon reaching the patient room 117 determines the imaging condition (menu for the object) and the like with the console device 17. He or she manually inputs the exposure condition in the source control unit 112, the exposure condition being equal to that corresponding to the imaging condition, or being after fine adjustment in compliance with a body size or the like of the patient P on the basis of the set imaging condition.

The operator OP positions the radiation source 111, the electronic cassette 16 and the patient P suitably. For example, the electronic cassette 16 is placed between the patient P and the bed 118. Then the radiation source 111 is driven to emit X-rays to the patient P. The X-rays transmitted through the patient P are detected by the electronic cassette 16, which generates a radiation image or X-ray image.

In the embodiment, the specific state of the electronic cassette 16 is defined in a state of movement of the electronic cassette 16. A period of the movement of the electronic cassette 16 is a period from selection of the main cassette by the operator OP in the storage room 116 and reception of information of the main cassette in the first radio communication unit 22 until setting the imaging condition (menu for the object) by the operator OP in the patient room 117 and reception of various data inclusive of the imaging condition in the first radio communication unit 22.

Figure 26:
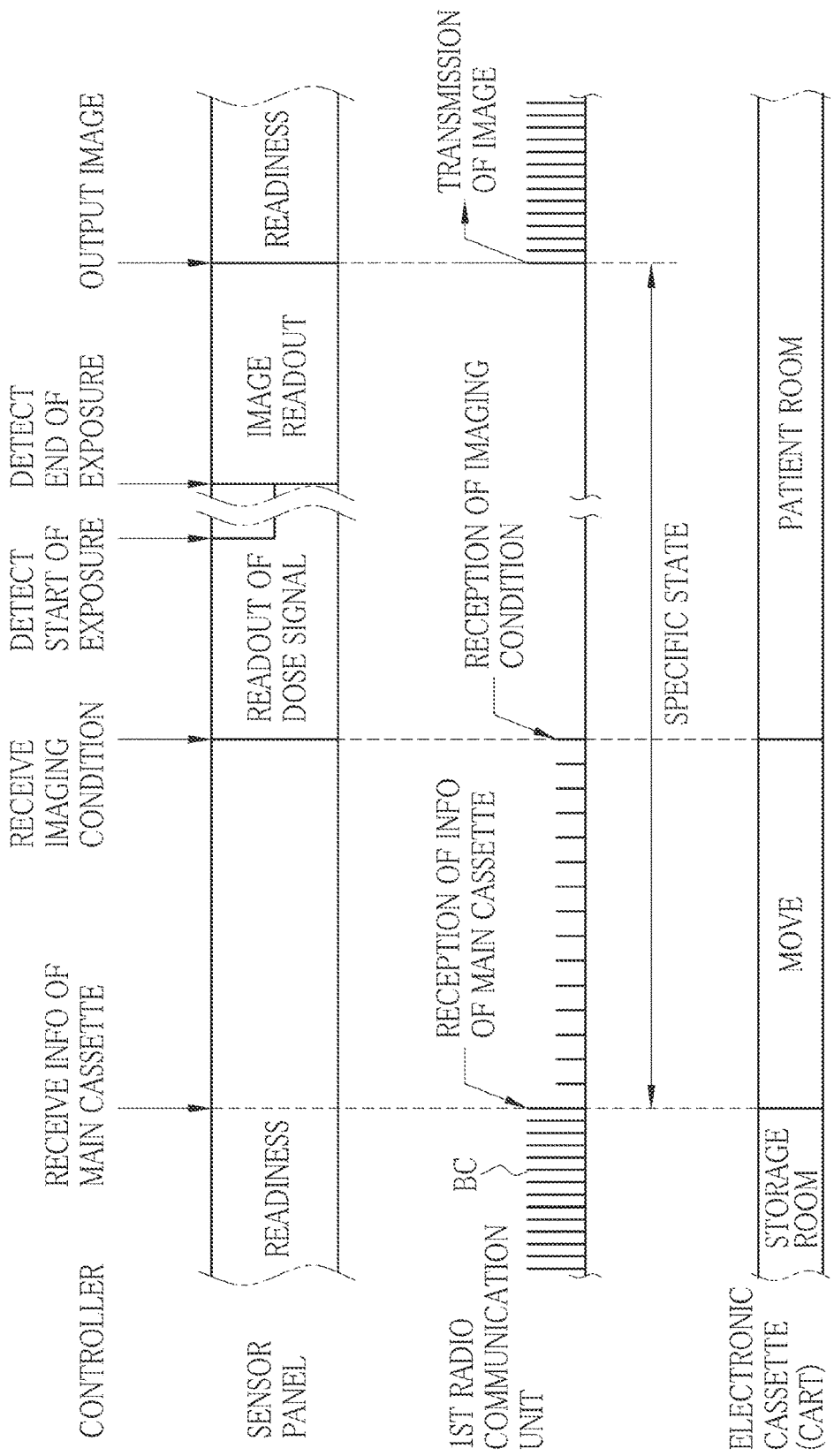
FIG. 26 is a timing chart illustrating a flow of a seventh preferred radiographic imaging apparatus.

In FIG. 26, the controller 68 changes the beacon BC in a period from reception of information of the main cassette in the first radio communication unit 22 until reception of various data including the imaging condition (menu for the object), by setting a beacon interval in the first radio communication unit 22 larger than a beacon interval in the non-specific state, and by setting radio signal strength of the beacon BC lower than radio signal strength of the beacon BC in the non-specific state. For example, the beacon interval is changed from approximately 100 msec to approximately 200 msec. The radio signal strength of the beacon BC is changed from a coverage area of a radius of 5 meters around the first radio communication unit 22 to a coverage area of a radius of 2 meters around the first radio communication unit 22.

Figure 27:
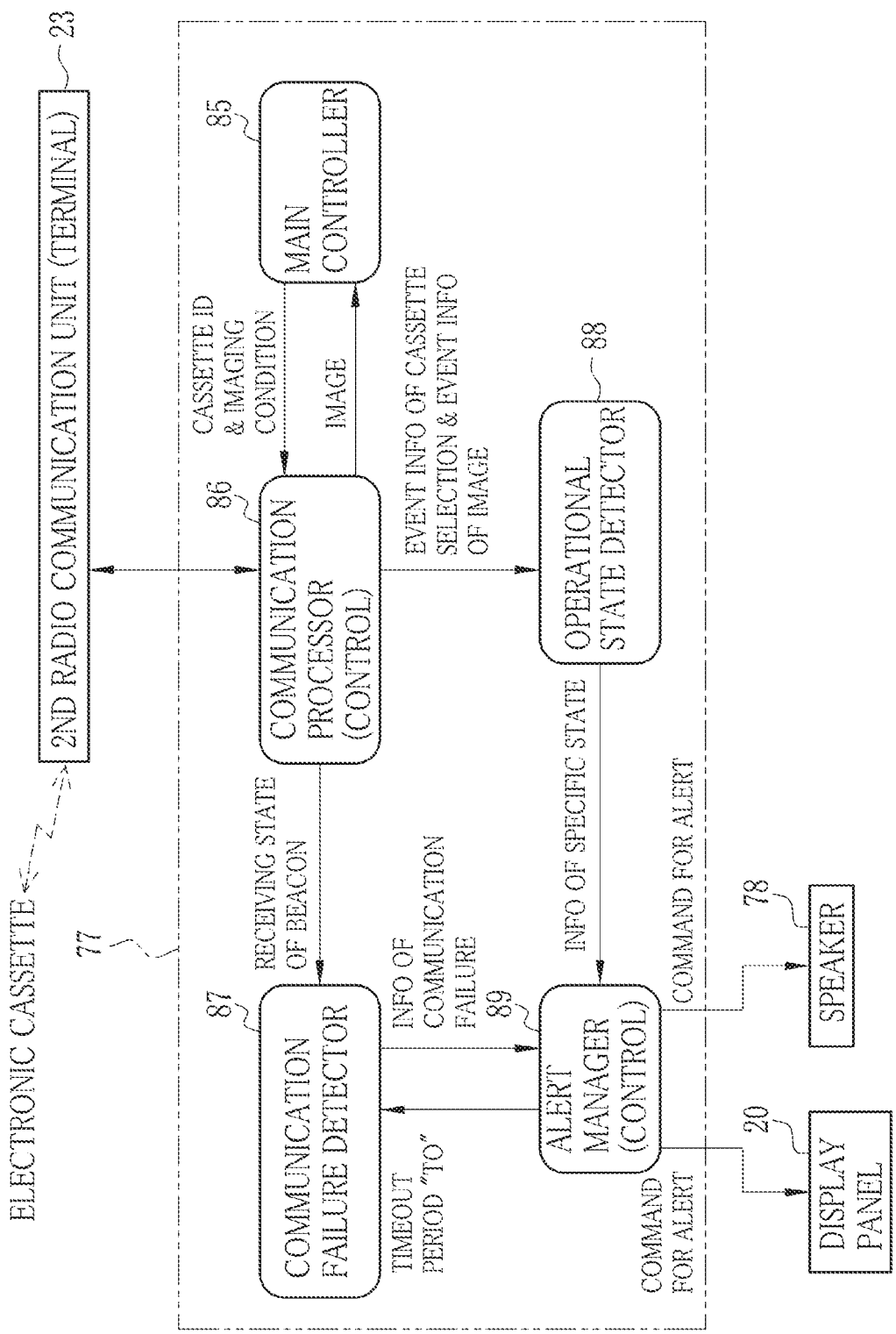
FIG. 27 is a block diagram schematically illustrating the CPU.

In FIG. 27, the communication processor 86 in the embodiment outputs event information of (transmission of) the cassette selection for the main cassette from the second radio communication unit 23 to the operational state detector 88, instead of the event information of the imaging condition (menu for the object) in the first embodiment. The operational state detector 88 judges that the electronic cassette 16 is in the specific state in a period from receiving the event information of the cassette selection in the communication processor 86 until receiving event information of (acquisition of) the radiation image. Succeeding steps after this are the same as those of the first embodiment.

Consequently, the power used for transmitting beacon BC while the electronic cassette 16 is moved can be reduced, because the beacon interval in the movement of the electronic cassette 16 is set larger than that while the electronic cassette 16 is in the non-specific state, and also the radio signal strength of the beacon BC is set lower than that in the non-specific state.

In the mobile imaging, the electronic cassette 16 and the console device 17 are positioned at a near distance while placed in the medical cart 110. Thus, the second radio communication unit 23 can receive the beacon BC even upon reducing the coverage area of the beacon BC by lowering the radio signal strength.

Furthermore, various other wireless terminal devices are disposed in a hospital facility in addition to the electronic cassette 16 and the console device 17. Interference of radio waves is likely to occur with the wireless terminal devices while the electronic cassette 16 is moved. However, risk of the interference with the wireless terminal devices can be reduced, as a coverage area of the beacon BC is reduced by increasing the beacon interval and by decreasing the radio signal strength of the beacon BC.

It is also possible to detect a state of the movement of the electronic cassette 16 while the medical cart 110 is moved. For example, an acceleration sensor is incorporated in the medical cart 110, to detect the state of the movement of the electronic cassette 16. A result of the detection is sent by the sensor to the electronic cassette 16 and the console device 17. In case the electronic cassette 16 receives the result of detection of the movement of the medical cart 110, the controller 68 regulates the beaconing of the beacon BC. In case the console device 17 receives the result of detection of the movement of the medical cart 110, the alert manager 89 avoids the generation of the alert notification. Furthermore, it is possible to detect the movement of the medical cart 110 (movement of the electronic cassette 16) in a period from actuation of lock mechanisms for the support column 114, the holder arm 115 and the radiation source 111 until release of the lock mechanisms.

Although the console device 17 is a structure discrete from the medical cart 110 in the embodiments, functions of the console device 17 can be incorporated in the medical cart 110 according to the invention.

Various constructions for the feature of the invention are possible in the scope of the invention. For example, information of the beacon interval or radio signal strength of the beacon BC after regulating the beaconing can be included in particular information transmitted from the first radio communication unit 22 to the second radio communication unit 23 in the regulation of the beacon BC in the controller 68 in the specific state, the particular information being the information of the end of the exposure in the fourth embodiment, or being the information of the sleep state in the sixth embodiment. Also, information of the beacon interval or radio signal strength of the beacon BC after regulating the beaconing can be superimposed with the beacon BC before the regulation and transmitted.

Also, one of the display panel 20 and the speaker 78, which are included in the alert indicator in the embodiment, can be omitted. Also, it is possible additionally to dispose a light source or vibrator for generating alert notification. The light source can be turned on for visible alert notification. The vibrator can be driven for vibration for a user to become aware of the alert notification by vibration.

Features of two or more of the above-described embodiments can be combined with one another. Also, radiation for use in the radiographic imaging can be gamma rays or the like instead of X-rays.

In one preferred embodiment mode of the invention, a radio communication method for a console device for communicative connection with an electronic cassette includes a step of receiving a beacon from the electronic cassette. It is checked whether a communication failure has occurred in the radio communication according to a receiving state of the beacon in the receiving step. Alert notification is generated to notify the communication failure while it is judged in the state checking step that the communication failure has occurred. It is checked whether the electronic cassette is in a predetermined specific state among plural operational states in relation to the beacon. Generation of the alert notification is avoided while it is judged in the state checking step that the electronic cassette is in the specific state.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiographic imaging apparatus, including an electronic cassette and a console device for radio communication with said electronic cassette, comprising:
    said electronic cassette including:
        a transmitter for transmitting a beacon for said radio communication;
        a regulation unit for regulating beaconing of said beacon in a predetermined specific state among plural operational states;
    said console device including:
        a receiver for receiving said beacon;
        a processor configured for:
            checking whether a communication failure has occurred in said radio communication according to a receiving state of said beacon in said receiver;
            checking whether said electronic cassette is in said specific state or in a non-specific state different from said specific state;
            validating generation of alert notification to notify said communication failure while said communication failure has occurred and said electronic cassette is in said non-specific state;
        an alert indicator for generating said alert notification in case that said processor validates generation of said alert notification.

2. A radiographic imaging apparatus as defined in claim 1, wherein while said electronic cassette is in said specific state, said processor does not check whether said communication failure has occurred.

3. A radiographic imaging apparatus as defined in claim 1, wherein while said electronic cassette is in said specific state, said processor disables said alert indicator.

4. A radiographic imaging apparatus as defined in claim 1, wherein information of a timeout period is stored previously, and said processor detects said communication failure assuming that interruption of reception of said beacon in said receiver has continued for said timeout period.

5. A radiographic imaging apparatus as defined in claim 4, wherein said timeout period is set longer while said electronic cassette is in said specific state than while said electronic cassette is in said non-specific state.

6. A radiographic imaging apparatus as defined in claim 1, wherein said electronic cassette includes a sensor panel having pixels for storing charge by detecting radiation transmitted through an object;
    said specific state is a state of image readout in which said sensor panel reads out said charge from said pixels for conversion into an image signal.

7. A radiographic imaging apparatus as defined in claim 6, wherein information of a timeout period is stored previously, and said processor detects said communication failure assuming that interruption of reception of said beacon in said receiver has continued for said timeout period;
    said timeout period is changed according to time taken for said image readout.

8. A radiographic imaging apparatus as defined in claim 7, wherein said electronic cassette is a selected one of at least a first electronic cassette and a second electronic cassette of which said time for said image readout is longer than said first electronic cassette;
    said timeout period associated with said second electronic cassette is longer than said timeout period associated with said first electronic cassette.

9. A radiographic imaging apparatus as defined in claim 1, wherein said specific state is a state of movement of said electronic cassette.

10. A radiographic imaging apparatus as defined in claim 1, wherein said specific state is a sleep state in which part of circuit devices in said electronic cassette is powered.

11. A radiographic imaging apparatus as defined in claim 1, wherein in said specific state, said regulation unit turns off said beacon.

12. A radiographic imaging apparatus as defined in claim 1, wherein said regulation unit sets a beacon interval of said beacon longer while said electronic cassette is in said specific state than while said electronic cassette is in said non-specific state.

13. A radiographic imaging apparatus as defined in claim 1, wherein said regulation unit sets a radio signal strength of said beacon lower while said electronic cassette is in said specific state than while said electronic cassette is in said non-specific state.

14. A radiographic imaging apparatus as defined in claim 1, wherein said electronic cassette detects a start of exposure of radiation, and said transmitter transmits a radiation image of an object to said receiver upon said exposure of said object to said radiation;
    said specific state is a state in a period from monitoring for detecting said start of said exposure of said radiation until transmission of said radiation image.

15. A radiographic imaging apparatus as defined in claim 1, wherein said electronic cassette detects an end of exposure of radiation, and said transmitter transmits a radiation image of an object to said receiver upon said exposure of said object to said radiation;
    said specific state is a state in a period from said detected end of said exposure of said radiation until transmission of said radiation image.

16. A radiographic imaging method in which radio communication is performed between an electronic cassette and a console device, comprising steps of:

transmitting a beacon for said radio communication from said electronic cassette;

regulating beaconing of said beacon in said electronic cassette in a predetermined specific state among plural operational states;

receiving said beacon in said console device;

checking whether a communication failure has occurred in said radio communication in said console device according to a receiving state of said beacon in said receiving step;

checking whether said electronic cassette is in said specific state or in a non-specific state different from said specific state in said console device;

validating generation of alert notification to notify said communication failure in said console device while said communication failure has occurred and said electronic cassette is in said non-specific state;

generating said alert notification in said console device in case that generation of said alert notification is validated.

17. A console device for radio communication with an electronic cassette, comprising:

a receiver for receiving a beacon from said electronic cassette;

a processor configured for:
checking whether a communication failure has occurred in said radio communication according to a receiving state of said beacon in said receiver;

checking whether said electronic cassette is in a predetermined specific state among plural operational states in relation to said beacon or in a non-specific state different from said specific state;

validating generation of alert notification to notify said communication failure while said communication failure has occurred and said electronic cassette is in said non-specific state;

an alert indicator for generating said alert notification in case that said processor validates generation of said alert notification.

* * * * *